(12) United States Patent
Barber et al.

(10) Patent No.: US 9,034,658 B2
(45) Date of Patent: May 19, 2015

(54) MICROFLUIDIC DEVICES FOR THE CAPTURE OF BIOLOGICAL SAMPLE COMPONENTS

(75) Inventors: Thomas A. Barber, Alston, MA (US); Ajay Shah, Cambridge, MA (US); John Walsh, Auburndale, MA (US); Mehmet Toner, Wellesley Hills, MA (US); Ravi Kapur, Sharon, MA (US); Shannon L. Stott, Stoneham, MA (US)

(73) Assignee: The General Hospital Corporation, Boston, MA (US)

( * ) Notice: Subject to any disclaimer, the term of this patent is extended or adjusted under 35 U.S.C. 154(b) by 491 days.

(21) Appl. No.: 13/511,536

(22) PCT Filed: Nov. 23, 2010

(86) PCT No.: PCT/US2010/057894
§ 371 (c)(1),
(2), (4) Date: Nov. 20, 2012

(87) PCT Pub. No.: WO2011/063416
PCT Pub. Date: May 26, 2011

(65) Prior Publication Data
US 2013/0209988 A1 Aug. 15, 2013

Related U.S. Application Data

(60) Provisional application No. 61/263,732, filed on Nov. 23, 2009.

(51) Int. Cl.
*G01N 33/543* (2006.01)
*G01N 33/574* (2006.01)
(Continued)

(52) U.S. Cl.
CPC .... *G01N 33/57492* (2013.01); *B01L 3/502753* (2013.01); *G01N 33/537* (2013.01);
(Continued)

(58) Field of Classification Search
CPC .......... G10N 33/57492; G10N 33/537; G10N 33/56972; B01L 3/502753
USPC ....................................................... 436/518
See application file for complete search history.

(56) References Cited

U.S. PATENT DOCUMENTS

| 6,083,709 A * | 7/2000 | Reynolds et al. ............ 435/7.94 |
| 2002/0042056 A1 * | 4/2002 | van Dongen et al. ............. 435/6 |

(Continued)

OTHER PUBLICATIONS

Nagrath et al. Isolation of rare circulating tumour cells in cancer patients by microchip technology, 207, Nature Letters, pp. 1235-1239.*

(Continued)

*Primary Examiner* — Melanie Y Brown
(74) *Attorney, Agent, or Firm* — Fish & Richardson P.C.

(57) ABSTRACT

Methods and systems for selectively capturing analytes, such as cells, e.g., circulating tumor cells (CTCs), from fluid samples are disclosed. The methods include contacting the sample with an analyte binding moiety that selectively binds to the analytes; optionally separating first components of the sample including a majority of the analytes bound to the binding moieties from second components of the sample using size-based separation, e.g., in a microfluidic channel; adding to the first components of the sample a plurality of binding agents under conditions that enable a plurality of the binding agents to be linked to the analyte binding moieties to form multivalent tagging agents bound to the analyte; passing the first components of the sample past a surface to which is attached a plurality of capture agents that selectively bind to the binding agents; and capturing the analytes by providing conditions that enable the multivalent tagging agents bound to the analytes to bind to one or more of the capture agents.

22 Claims, 33 Drawing Sheets

(51) Int. Cl.
  *B01L 3/00* (2006.01)
  *G01N 33/537* (2006.01)
  *G01N 33/569* (2006.01)
  *G01N 15/14* (2006.01)

(52) U.S. Cl.
  CPC ... *G01N33/56972* (2013.01); *B01L 2300/0816* (2013.01); *B01L 2400/0487* (2013.01); *B01L 2400/086* (2013.01); *G01N 15/1484* (2013.01)

(56) References Cited

U.S. PATENT DOCUMENTS

| | | | |
|---|---|---|---|
| 2005/0032126 A1 | 2/2005 | Coombs et al. | |
| 2006/0134599 A1 | 6/2006 | Toner et al. | |
| 2007/0059680 A1 | 3/2007 | Kapur et al. | |
| 2007/0099207 A1* | 5/2007 | Fuchs et al. | 435/6 |
| 2007/0202536 A1* | 8/2007 | Yamanishi et al. | 435/7.1 |
| 2008/0057505 A1* | 3/2008 | Lin et al. | 435/6 |
| 2008/0138809 A1 | 6/2008 | Kapur et al. | |
| 2008/0261829 A1* | 10/2008 | Harvey et al. | 506/13 |
| 2008/0318203 A1* | 12/2008 | Tran et al. | 435/2 |
| 2013/0337500 A1* | 12/2013 | Tan et al. | 435/39 |
| 2014/0087456 A1* | 3/2014 | Lim et al. | 435/309.1 |

OTHER PUBLICATIONS

International Search Report and Written Opinion issued Aug. 11, 2011 in international application No. PCT/US2010/057894, 12 pgs.

* cited by examiner

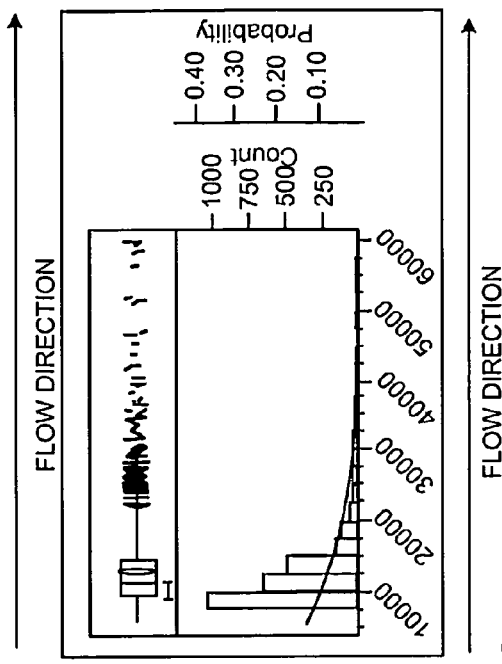
FIG. 4C
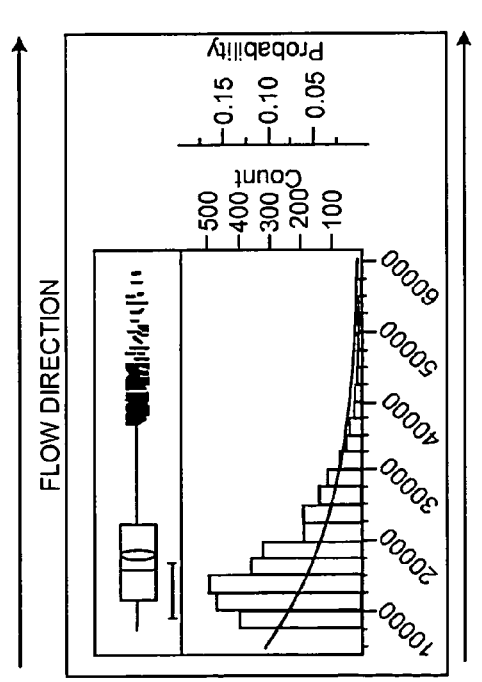
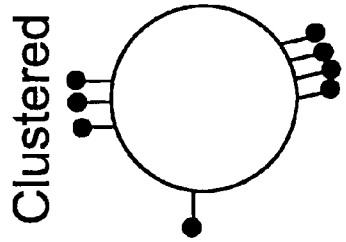
FIG. 4D

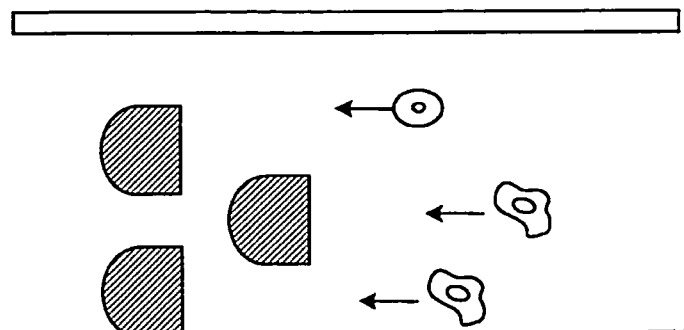
FIG. 5E
FIG. 5F
half-post lattice
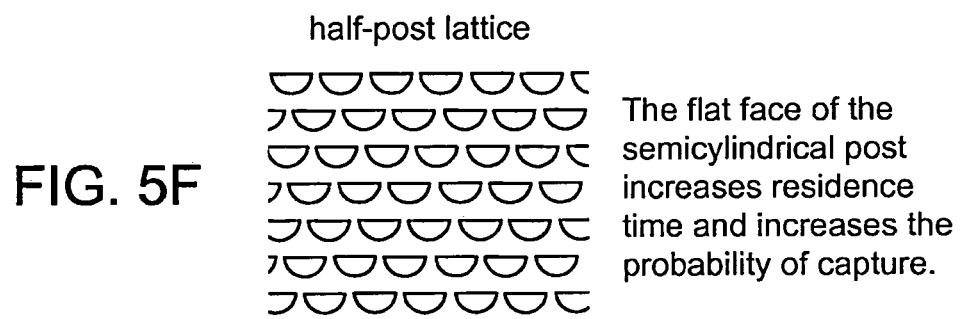
The flat face of the semicylindrical post increases residence time and increases the probability of capture.
FIG. 5G
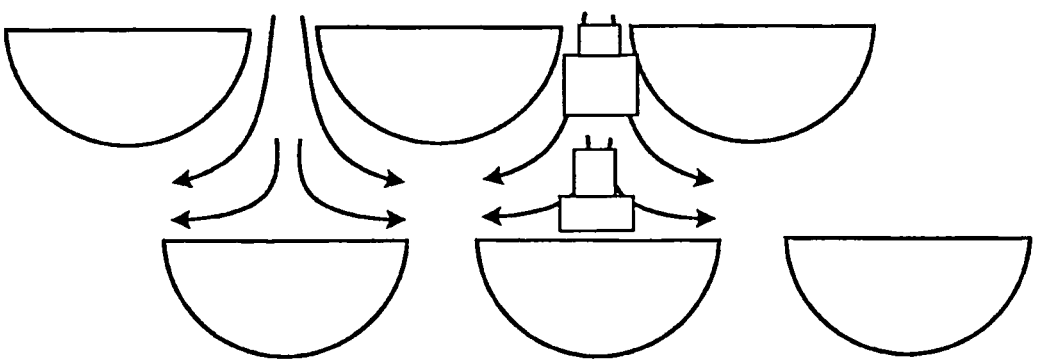

Rotated hexagonal Lattice

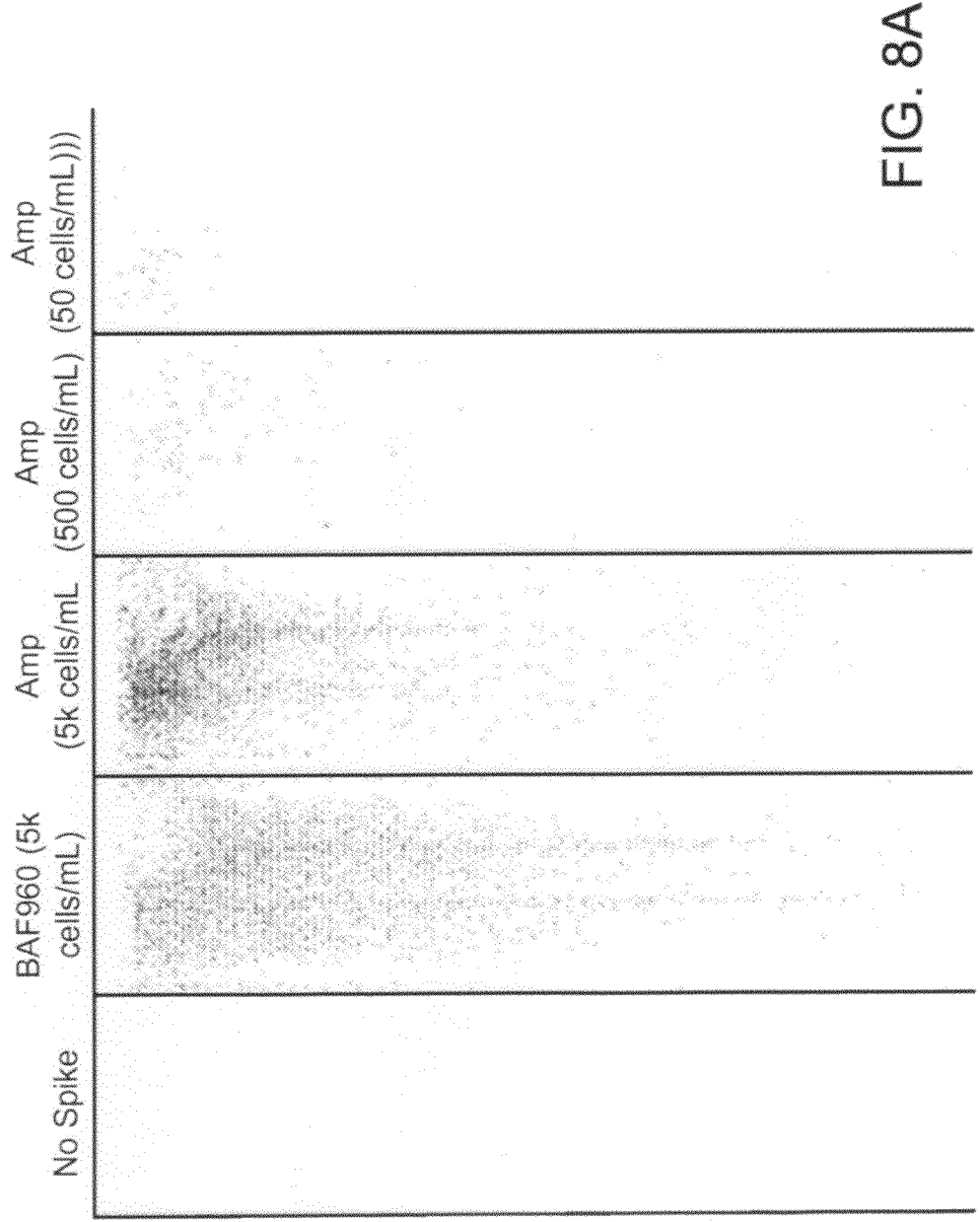

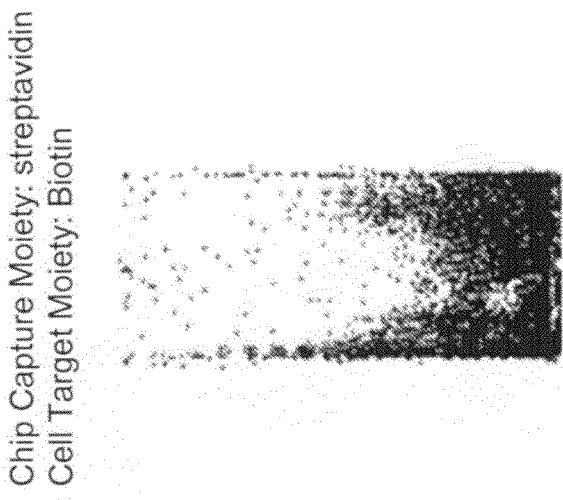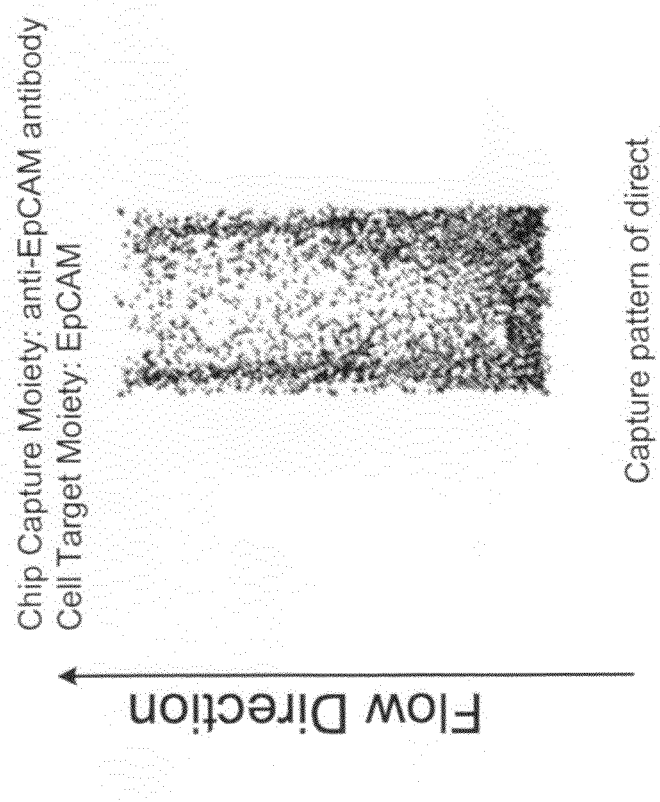

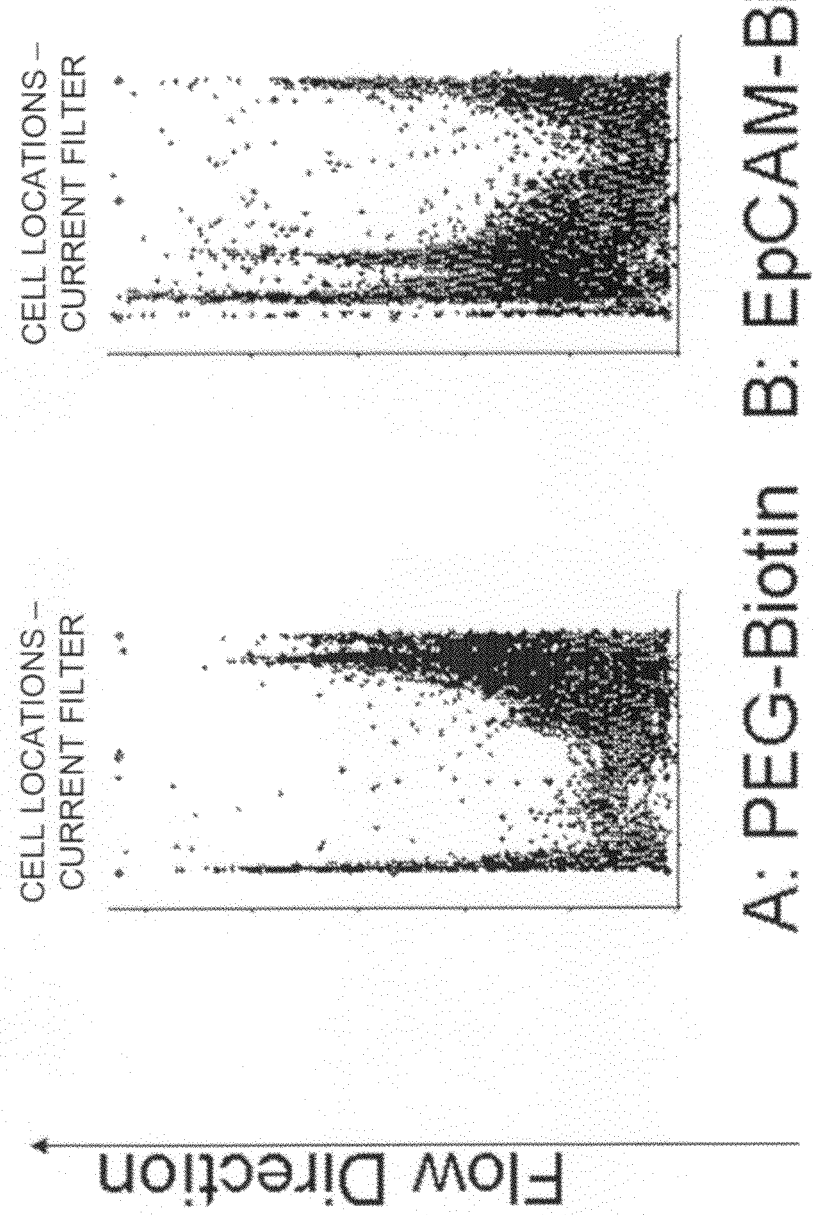

MICROFLUIDIC DEVICES FOR THE CAPTURE OF BIOLOGICAL SAMPLE COMPONENTS

CROSS-REFERENCE TO RELATED APPLICATIONS

This application is a §371 application of international application no. PCT/US2010/057894, filed Nov. 23, 2010, which claims priority to U.S. Patent Application No. 61/263,732 (Barber et al.), filed on Nov. 23, 2009, the entire contents of which are incorporated herein by reference. In addition, the following patent applications are also incorporated herein by reference in their entireties: U.S. Published Patent Application No. 2006-0134599 filed on Dec. 19, 2005; U.S. Published Patent Application No. 2007-0026381 filed on Jun. 8, 2006; PCT International Patent Application No. WO2009/051734 filed on Oct. 16, 2008; and PCT International Patent Application No. WO2004/029221 filed on Sep. 29, 2003.

FIELD OF THE INVENTION

This disclosure relates to the selective capture of components, such as living cells, from biological samples, such as blood.

BACKGROUND

The isolation of specific cell populations from complex mixtures such as whole blood has significant utility in both clinical practice and basic medical research. A variety of approaches can be used to separate cells from a heterogeneous sample. For example, some techniques can use functionalized materials to capture cells by binding cell surface markers that are particular to the target cell population. The functionalized materials can include surface-bound capture moieties such as antibodies or other specific binding molecules, such as aptamers or selectins.

Viable tumor-derived epithelial cells (e.g., circulating tumor cells or CTCs) have been identified in peripheral blood from cancer patients and are likely the origin of intractable metastatic disease. The isolation of CTCs represents a potential alternative to invasive biopsies as a source of tumor tissue for the detection, characterization, and monitoring of non-hematologic cancers. The ability to identify, isolate, propagate, and molecularly characterize CTC subpopulations could further the discovery of cancer stem cell biomarkers and expand the understanding of the biology of metastasis. Current strategies for isolating CTCs are limited to complex analytic approaches that generate very low yield and purity. CTCs are considered to be rare, making up as few as about 1 CTC per $10^9$ hematologic cells in the blood of patients with metastatic cancer. Thus, the isolation of CTCs from blood samples presents a tremendous technical challenge.

Microfluidic lab-on-a-chip devices can be used for cell sorting and rare cell detection. Such devices have been used for microfluidic flow cytometry, continuous size-based separation, and chromatographic separation. For example, a microfluidic affinity-based chip that is configured to isolate CTCs from the whole blood of cancer patients is described, e.g., in Nagrath et al., "Isolation of rare circulating tumor cells in cancer patients by microchip technology," Nature 450: 1235-1239 (2007). CTCs may disseminate from the tumor and are observed to be present in numbers that tend to correlate with patients' clinical courses. CTCs may also be involved in metastasis. Accordingly, such microfluidic chip technology can be used in diagnostic and prognostic devices for oncological applications.

However, the capture of CTCs from a blood sample on the surface of a microfluidic channel using surface-bound antibodies, such as an anti-Epithelial Cell Adhesion Molecule (EpCAM) antibody can be difficult due to both the rarity of the CTCs in the sample and/or reduced levels of CTC expression of the antigen corresponding to the surface-bound antibody. Accordingly, there remains a need for methods and devices for improving the detection levels of CTCs in biological samples.

SUMMARY

This disclosure provides methods and microfluidic devices for isolating analytes from a fluid sample, including the selective capture of analytes such as circulating tumor cells (CTCs) or other types of cells within a microfluidic channel. The new methods and systems are useful to amplify and isolate low antigen expressing cells, which may be quite rare within a sample, or may be abundant in the sample, but are still otherwise hard to isolate because of the very low expression of any specific antigen(s) on their surface.

The invention is based, at least in part, on the discovery that capture of analytes, e.g., CTCs, from a biological sample (e.g., blood) can be significantly enhanced by combining the sample with a multivalent tagging agent that includes two parts. The first part is a selective analyte binding moiety, e.g., a moiety that selectively binds to an analyte, e.g., EpCAM expressed on the surface of CTCs. The second part is a plurality of binding agents, e.g., 2 to 10 or more binding agents, such as biotin molecules, that are each linked or coupled to each analyte binding moiety. Once the multivalent tagging agents are bound to the analytes of interest, the sample is flowed along a surface to which is bound one or more capture agents to capture the multivalent tagging agent. The capture agent includes a ligand that binds, e.g., binds strongly, to the binding agents of the multivalent tagging agent (e.g., the ligand can be a surface-bound biotin-binding conjugate, such as surface-bound avidin or streptavidin).

The new methods provide much higher capture efficiencies than methods using direct biotinylation, which can bind approximately the same number of biotin molecules to the surface of an analyte as the methods disclosed herein, but does not work nearly as well to capture, separate, or isolate analytes in microfluidic devices as described herein. Without wishing to be bound to a theory, applicants believe that the present methods provide the binding agents in a superior conformation and clustered configuration for capture by the conjugate capture agents than other known methods. The present methods enable the simple deposition of clusters of binding agents, such as biotin molecules, on the surface of analytes, such as cells like CTCs, in a way that ensures that the binding agents are accessible and in a preferred configuration for cell capture in microfluidic devices. Thus, the present methods are highly selective and sensitive to rare cells, such as CTCs, including CTCs that have a low expression of antigens such as EpCAM, and any cells that have a low expression of distinguishing surface antigens.

In one aspect, methods of selectively capturing analytes, such as cells, e.g., tumor cells, such as circulating tumor cells (CTCs), from a sample, e.g., a fluid sample, such as a biological sample, e.g., whole blood, include contacting the sample with an analyte binding moiety that selectively binds to the analytes; optionally separating first components of the sample including a majority of the analytes bound to the binding moieties from second components of the sample using size-based separation, e.g., in a microfluidic channel; adding to the first components of the sample a plurality of binding agents under conditions that enable a plurality of the binding agents to be linked to the analyte binding moieties to form multivalent tagging agents bound to the analyte; passing the first components of the sample past a surface to which is attached a plurality of capture agents that selectively bind to the binding agents; and capturing the analytes by providing conditions that enable the multivalent tagging agents bound to the analytes to bind to one or more of the capture agents.

In another aspect, the invention features methods of selectively capturing tumor cells from whole blood. The methods include contacting the whole blood with a binding moiety that selectively binds to an antigen expressed on a surface of the tumor cells and not on a surface of normal cells to form tumor cell-binding moiety complexes; separating a first subsample comprising tumor cell-binding moiety complexes and white blood cells from a second subsample comprising red blood cells, platelets, and unbound binding agent using size-based separation; adding to the first subsample a plurality of binding agents under conditions that enable a plurality of the binding agents to be linked to the binding moieties bound to the tumor cells; passing the first subsample past a surface to which is attached a plurality of capture agents that selectively bind to the binding agents; and capturing the tumor cells by providing conditions that enable the binding agents bound to the tumor cells to bind to one or more of the capture agents.

Embodiments of these inventions can include one or more of the following features.

In some embodiments, the multivalent tagging agent includes an analyte binding moiety that includes an antibody bound to Horse Radish Peroxidase (HRP). In some cases, the cell expresses EpCAM and the HRP-antibody binds to EpCAM. In some cases, forming a multivalent tagging agent includes adding another binding agent, e.g., tyramide-biotin, to the first subsample containing the analyte binding moieties (at least some of which are bound to the analytes in the sample).

In some embodiments, the analyte is a cell, e.g., a tumor cell. In some cases, the cell expresses EpCAM and the multivalent selective tagging agent binds to EpCAM. In some cases, the binding agents include biotin. In some embodiments, the capture agent includes a ligand that binds to biotin. In some cases, the cells express EpCAM and the biotinylated antibody binds to EpCAM.

In some embodiments, methods also include contacting the multivalent tagging agent with the capture agent within a channel formed by at least a portion of the surface attached to the capture agent.

In some embodiments, analytes or tumor cells have a concentration of less than about $10^{-6}$/mL in the fluid sample, e.g., whole blood. In some cases, the surface is an outer surface of a post within the channel, the post extending partially across the channel in a direction perpendicular to a direction of fluid flow of the biological sample within the channel.

In some embodiments, the sample is a biological sample, such as blood, e.g., whole blood, urine, saliva, plasma, lung washings, or lymph. In some cases, the first components of the biological sample comprise white blood cells.

In some embodiments, methods also include separating unbound multivalent selective binding agent from the first components of the biological sample while separating the first components of the biological sample from the second components of the biological sample.

The structure of the multivalent tagging agent and the amount of the multivalent tagging agent added to the biological sample containing the analyte can be selected to form a complex containing an analyte (e.g., a cell such as a CTC) bound to the multivalent tagging agent. For example, a biotinylated EpCAM antibody containing two or more biotin moieties can be added to a blood sample containing CTCs to form a CTC complex. The CTC complex can include enough biotin molecules to permit capture of the CTC cell complex with a separate biotin-binding capture agent bound to a surface (e.g., a streptavidin-coated surface). Alternatively, the complex could be captured via one of the other tagging agents present in the complex.

An analyte-tagging agent complex (e.g., a CTC bound to a biotinylated EpCAM antibody linked to multiple biotin binding agents) can be captured from the biological sample within a microfluidic channel. The channel can include a surface configured to capture the multivalent tagging agent from the biological sample within the channel, including the CTC cell complex. For example, the surface can include a biotin-binding capture agent bound to the surface.

The surface can enclose a microfluidic channel (e.g., a channel with at least one dimension less than about 1 mm) with one or more posts positioned within the channel. The posts can have one or more surfaces presenting a conjugate capture agent that binds to the multivalent binding agent. The dimensions and positions of the posts can be configured to capture an analyte in the fluid sample within the microfluidic channel, while permitting the fluid sample to pass through the microfluidic channel at a desired flow rate (e.g., the arrangement and dimensions of the posts can be selected to prevent undesirably high levels of resistance to fluid flow through the microfluidic channel). The posts within the channel can include a hemispherical cross-sectional dimension, with a flat portion of the surface oriented substantially perpendicular to a direction of fluid flow of the biological sample within the channel. The post can extend completely or partially across the channel, and can include a top surface configured to capture the multivalent binding agent within the channel. The channel can include a gap between a post and a channel wall, such as a gap having a width that is on the order of the size of an analyte (e.g., a 10 micron gap). The posts can extend from a channel wall and terminate within the channel at a distance from the nearest channel wall of up to about 50% of the distance across the channel in the direction of the post (e.g., including a distance of 40%, 30%, 20% or 10% of the distance across the channel).

This disclosure also describes the discovery that the capture of other components of a sample besides the analyte or multivalent tagging agent (i.e., "non-specific binding" or NSB) on a surface with a conjugate capture agent can be reduced by contacting the surface with a nonionic surfactant prior to and after contacting the surface with the biological sample. In particular, in a first example, non-specific binding of components of a biological sample (i.e., cells other than CTCs) to a biotin-binding surface was reduced by first contacting the surface with a polysorbate 20 surfactant before contacting the surface with the sample containing the multivalent tagging agent (e.g., biotinylated anti-EpCAM antibodies). In a second example, non-specific binding of components of a sample to the surface was reduced by contacting the surface with a polysorbate 20 surfactant after contacting the surface with the sample containing the multivalent tagging agent.

The captured surface-bound analytes can be released. For example, a viable cell can be captured on a surface and later released. In one method, a CTC is initially bound to a multivalent tagging agent in a blood sample, the blood sample is passed through a microfluidic channel where the CTC is captured by a surface of a microfluidic channel having a surface-bound conjugate capture agent, the remaining portion of the biological sample is removed from the channel, and then the CTC is subsequently released from the surface. The analyte can be released, for example, by dissociating the analyte and the multivalent tagging agent, and/or dissociating the multivalent tagging agent and the conjugate capture agent. For example, release of the CTC from the surface can occur in response to a changed condition in the microfluidic channel such as a change in pH, ionic strength, temperature, or introduction of another material in the channel that interrupts the binding of the analyte and the multivalent tagging agent, and/or binding of the multivalent tagging agent and the conjugate capture agent.

A captured cell population within a microfluidic channel can be detected, for example, by lysing the cell population within the channel and measuring RNA obtained therefrom. The cells can be imaged and counted, e.g., manually, to evaluate the purity of the captured cell population. Purity count can be performed on a fluorescent microscope, e.g., by manually counting the imaged cells (e.g., fluorescently labeling the cells to gauge purity).

The term "multivalent tagging agent" refers to a material configured to bind to (e.g., chemically associate with, e.g., form a releasable chemical bond, such as a hydrogen bond, or a covalent bond) both a specific analyte and a capture agent. The multivalent tagging agent includes two parts. The first part is a selective analyte binding moiety that selectively or preferentially binds to a specific analyte, but does not bind, or binds with a lower affinity, to other molecules that may be present in a sample. The second part is a plurality of two or more binding agents that are each linked to the analyte binding moiety by a molecular linker. For example, the multivalent tagging agent can include an anti-EpCAM antibody that can bind to a CTC and a set of biotin molecules as the binding agents. These binding agents can then be bound to a capture agent that is, for example, attached to a surface of a solid substrate or a bead. The multivalent tagging agent can be configured to bind to itself or to other materials present in a sample in addition to the analyte and the conjugate capture agent, so as to form a network around an analyte enabling a surface-bound capture agent to capture the analyte by binding to any one of many different binding agent molecules present in the network.

The term "conjugate capture agent" or "capture agent" refers to a material configured to bind to the binding agents on the multivalent tagging agent. Thus, the capture agent includes a ligand that binds to the binding agent. In some embodiments, the capture agent ligand binds to the binding agent with a dissociation constant that is lower than the dissociation constant between the analyte binding moiety and the analyte. One particular example of a useful capture agent includes a ligand that binds to biotin. The capture agents can include only the ligand (if the ligand can be directly bound to a surface), or they can include the ligand and some molecular linker to bind the ligand to a surface.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

Further objects, features and advantages of the invention will become apparent from the following detailed description taken in conjunction with the accompanying figures that illustrate embodiments, results, and/or features of certain embodiments of the present invention.

FIGS. 4A-4D are, respectively flow concentrations, capture heat maps, capture histograms, and schematic diagrams of single cells that compare the capture efficiency of target cells amplified using different approaches.

FIGS. 5E and 5F are plan views that show two different arrays of posts having a non-circular cross section and being positioned within a microfluidic channel. FIG. 5G is a schematic showing fluid flow lines around a non-circular post within a microfluidic channel.

FIG. 8A is a series of capture heat maps that show the position of captured cells within a microchannel.

FIGS. 11A and 11B are capture heat maps that show the position of CTCs captured within a microchannel for direct immuno-capture (i.e., using a surface-bound EpCAM antibody to capture the CTCs in the microchannel) (FIG. 11A) or pre-tagged capture (i.e., using a surface-bound streptavidin to bind CTC complexes comprising a CTC, biotinylated EpCAM antibody, biotin and streptavidin (FIG. 11B)). A majority of the cells in FIG. 11B were captured in the first ⅓ of the chip with pre-tagged CTCs and surface-bound streptavidin, showing a much higher efficiency relative to untagged capture of CTC with EpCAM antibody shown in FIG. 11A.

Figure 12C:
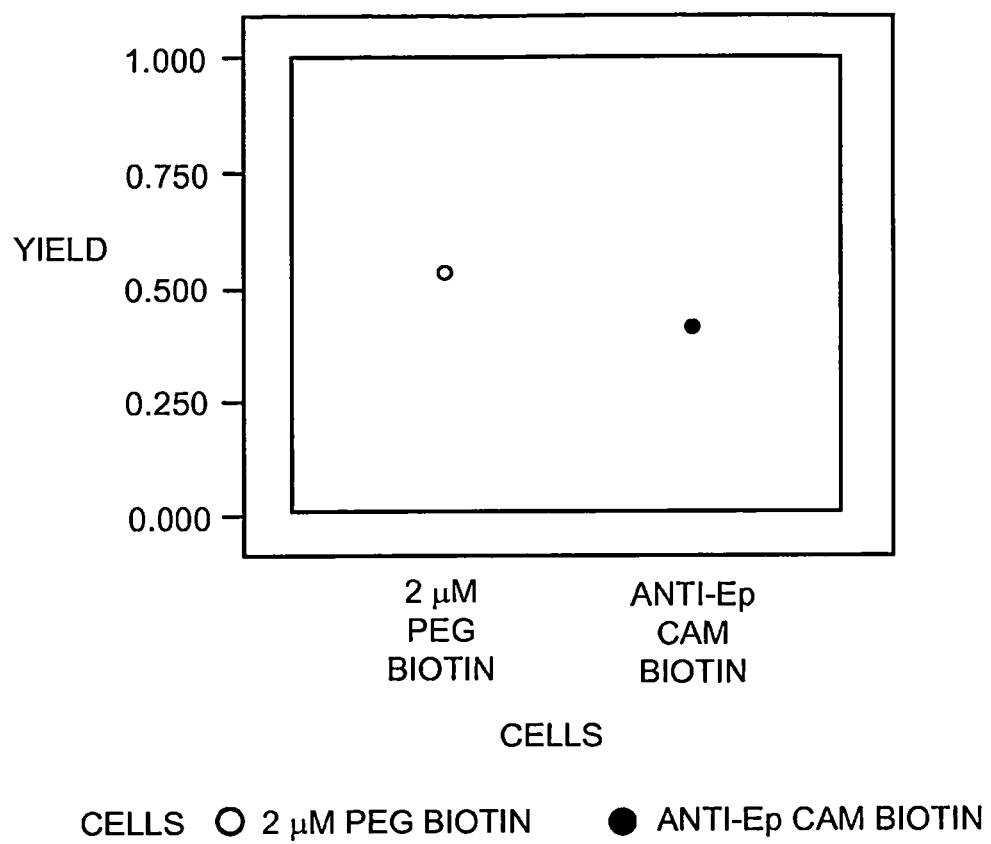

FIGS. 12A and 12B are capture heat maps that show the position of CTCs captured in flow cells using Neutravidin modified surfaces to capture specifically (EpCAM-mediated) and nonspecifically (NHS-PEG-Biotin) biotinylated cells. FIG. 12C shows that cells can be biotinylated with varying levels of specificity using different dimensions of the targets (NHS-PEG-Biotin modifying cell surface amine groups, biotinylated anti-EpCAM modifying cell surfaces EpCAM).

Figure 13:
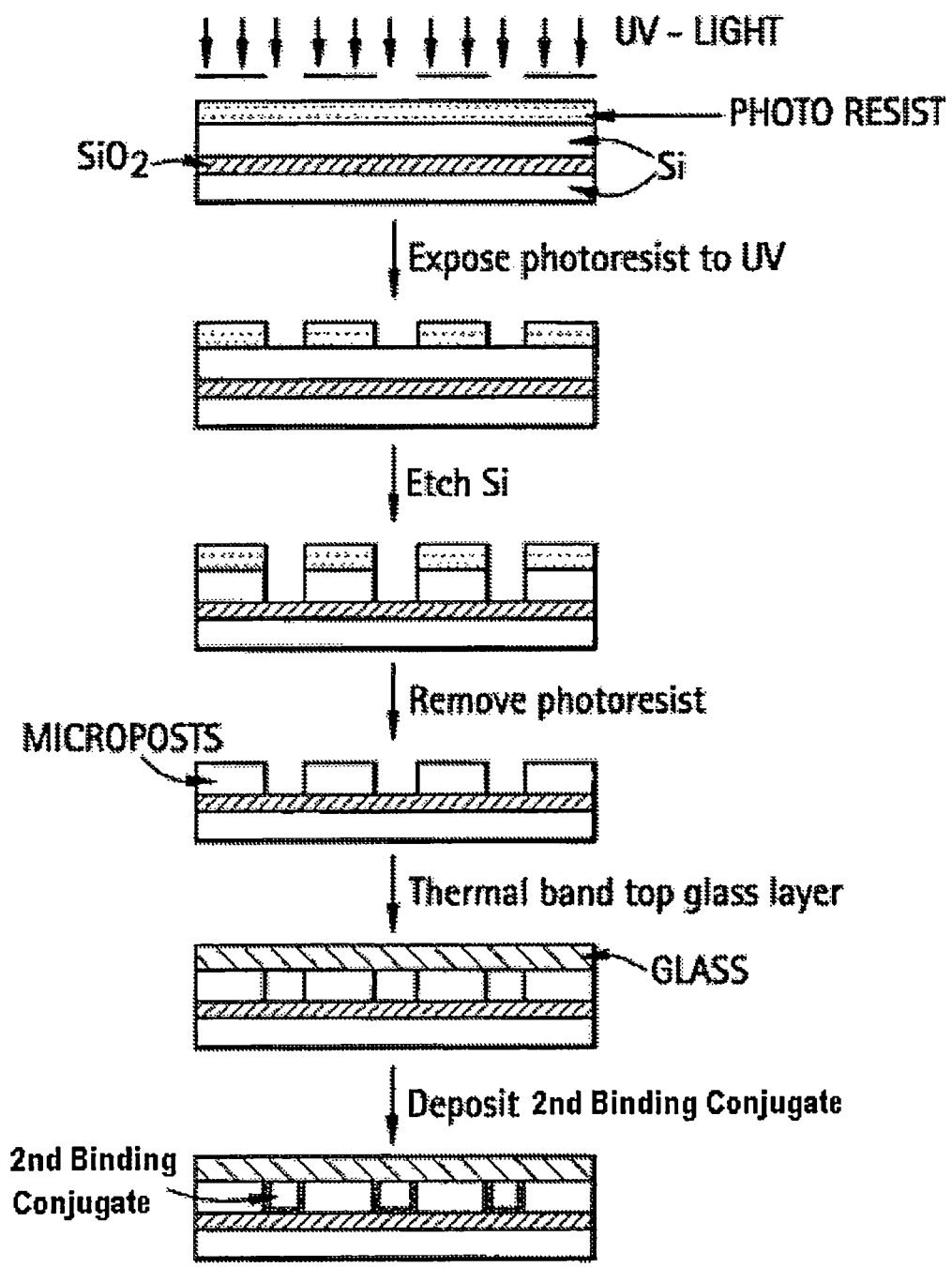

FIG. 13 is a schematic showing one method for forming the microfluidic channel devices disclosed herein.

Figure 14:
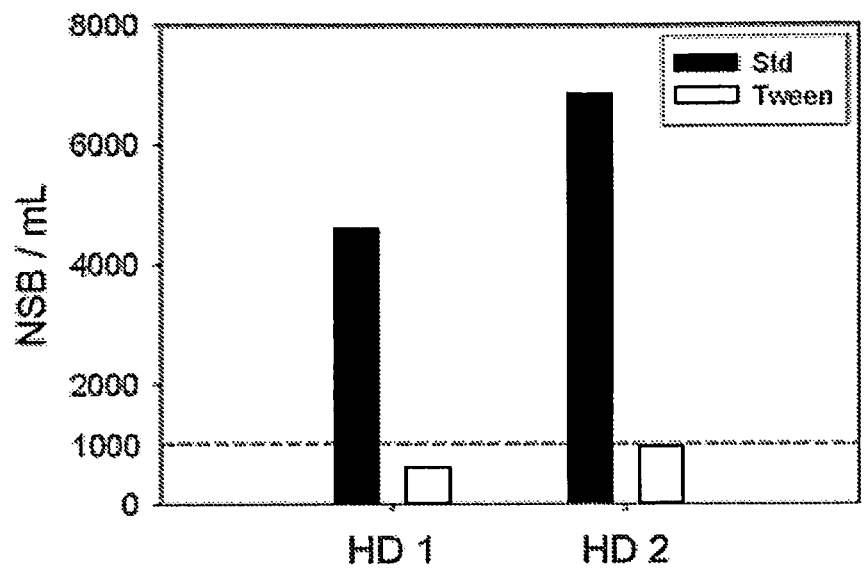

FIG. 14 is a graph of data showing the reduction of non-specific binding on the surface of a microfluidic channel coated with anti-EpCAM antibodies for capture of circulating tumor cells.

Figure 15:
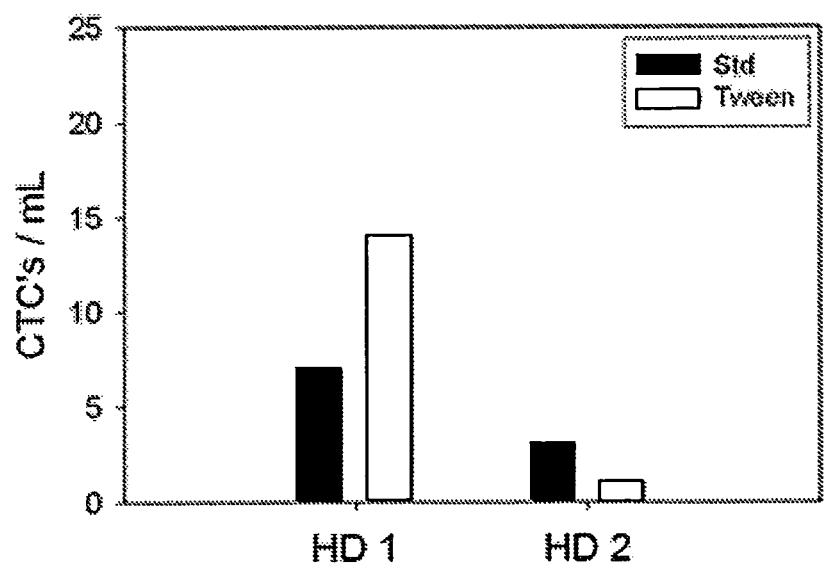

FIG. 15 is a graph of data showing a reduction in "false positives" in the data shown in FIG. 14.

Figure 16:
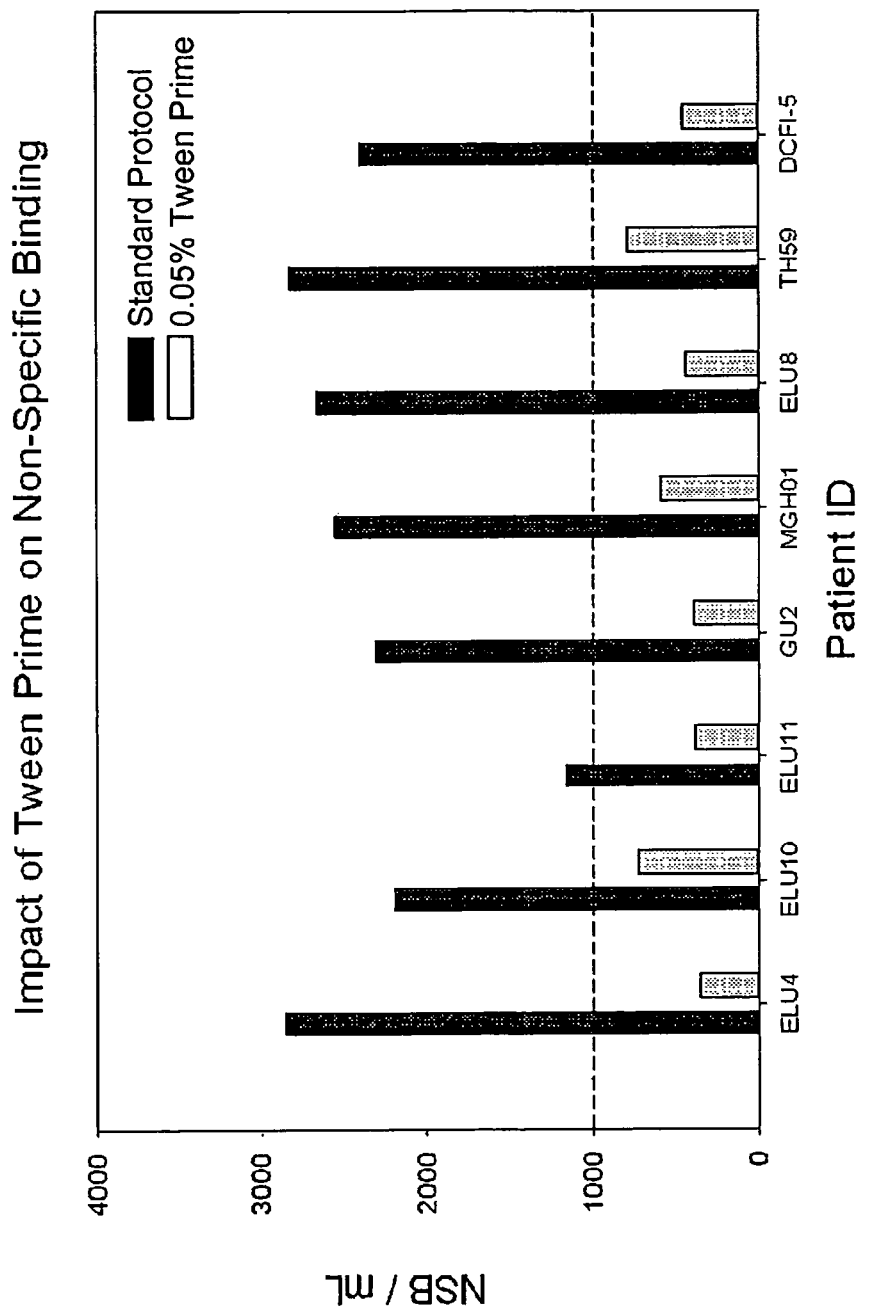

FIG. 16 is a graph of data showing the reduction of non-specific binding on the surface of a microfluidic channel coated with anti-EpCAM antibodies for capture of circulating tumor cells.

Figure 17:
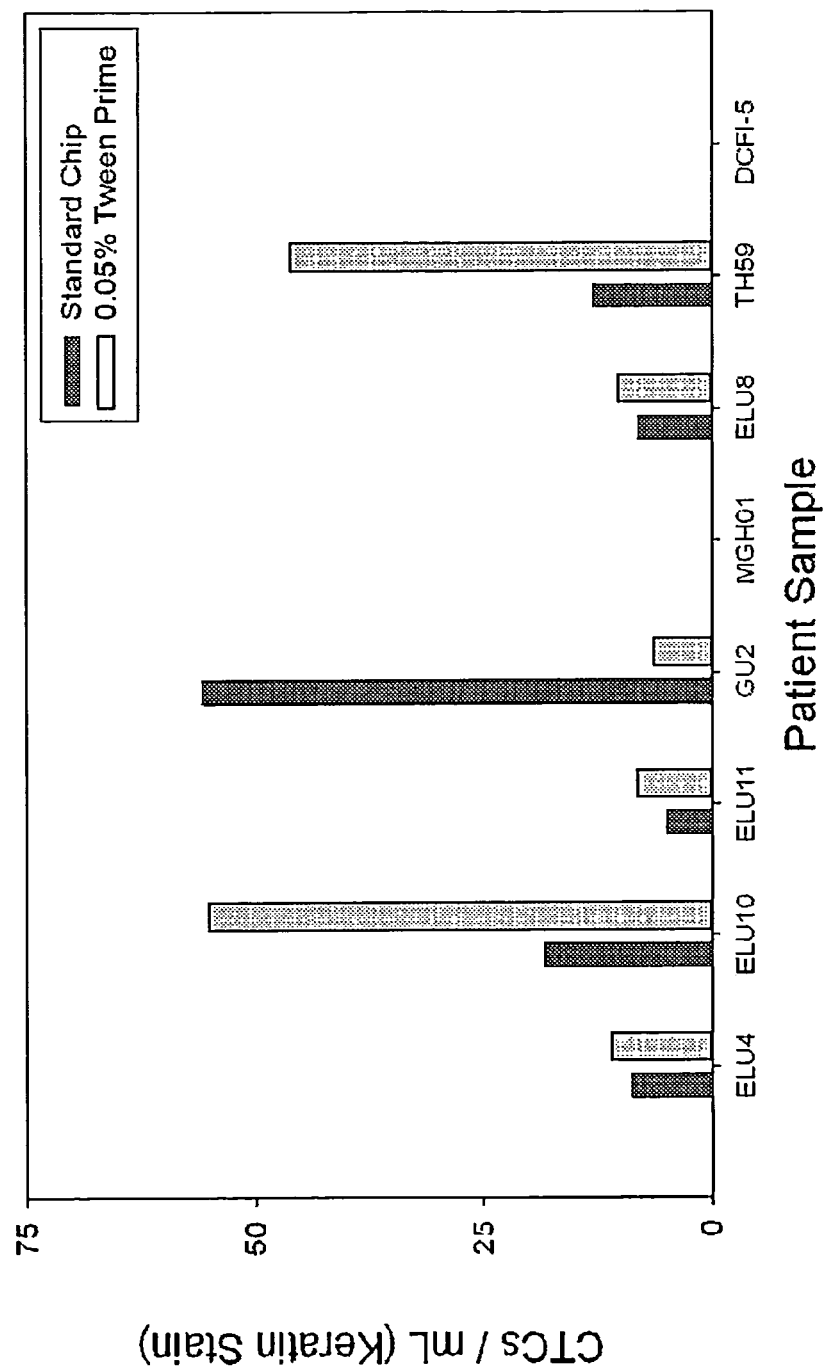

FIG. 17 is a graph of data showing the reduction of non-specific binding after pre-washing the surface of a microfluidic channel coated with anti-EpCAM antibodies with polysorbate 20 prior to contacting the channel surface with a sample for capture of circulating tumor cells in the sample.

Figure 18:
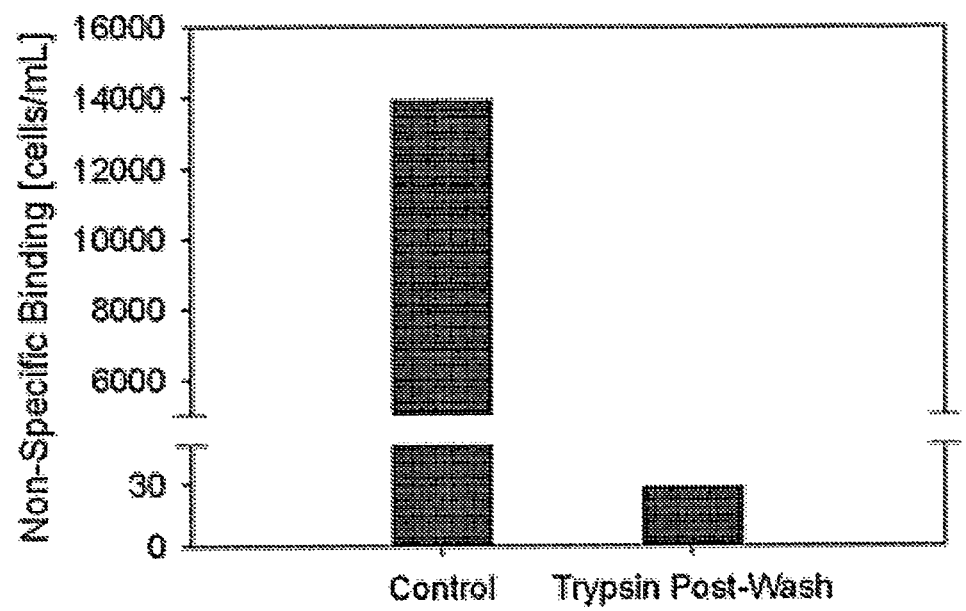

FIG. 18 is a graph of data showing a reduction of non-specific binding in a healthy donor control microfluidic channel by washing the bound analyte cells with a polysorbate20 solution after cell-binding to the channel.

Figure 19:
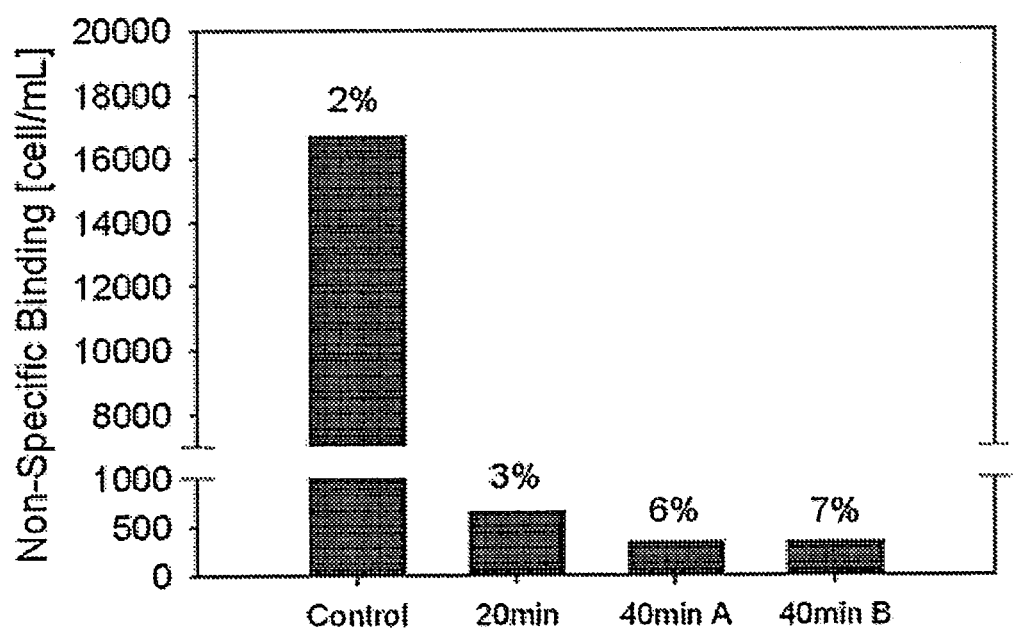

FIG. 19 is a graph of data showing a reduction of non-specific binding in a healthy donor control microfluidic channel by washing the bound analyte cells with a polysorbate20 solution after cell-binding to the channel.

Figure 20A:
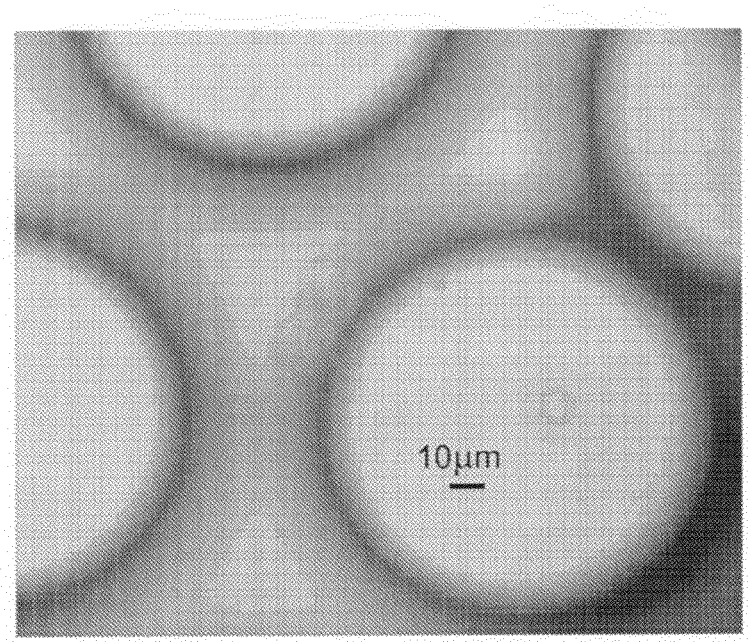
Figure 20B:
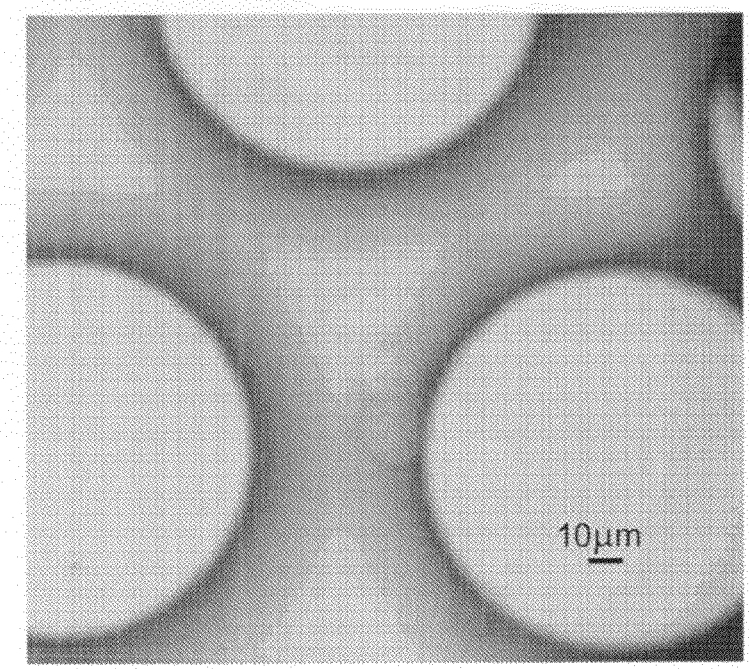

FIGS. 20A and 20B are representative micrographs illustrating the condition of spiked cells in the tween post-wash chip (20A) and control chip (20B).

Figure 21A:
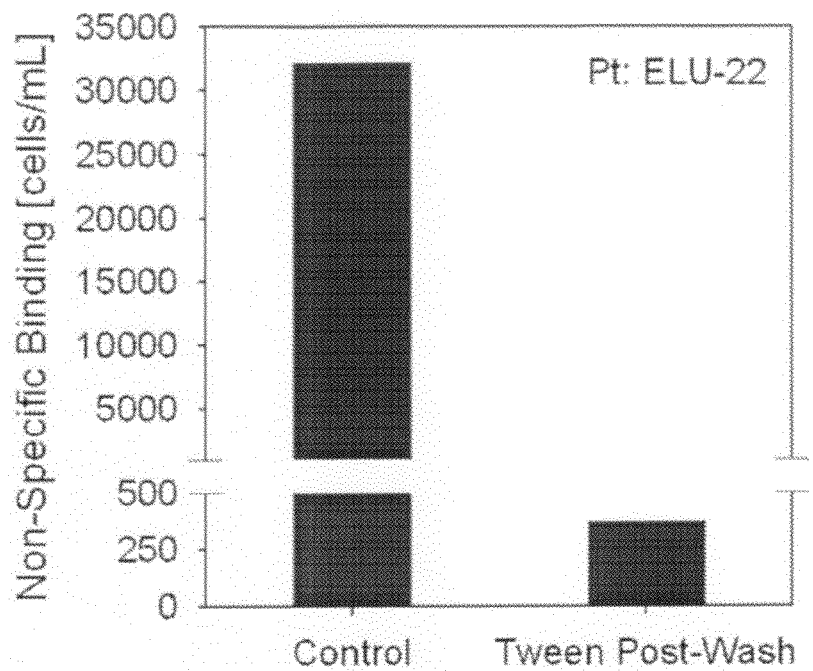
Figure 21B:
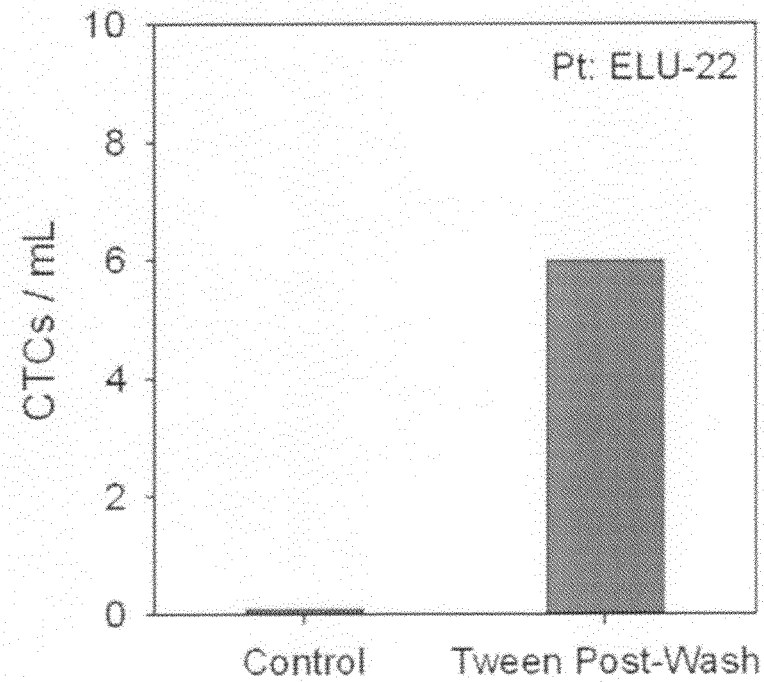

FIG. 21A is a graph of data showing the reduction in non-specific binding in an early stage lung cancer patient. FIG. 21B is a graph of data showing the increase in target cell capture in the tween post-wash chip in comparison to the control chip.

Figure 22A:
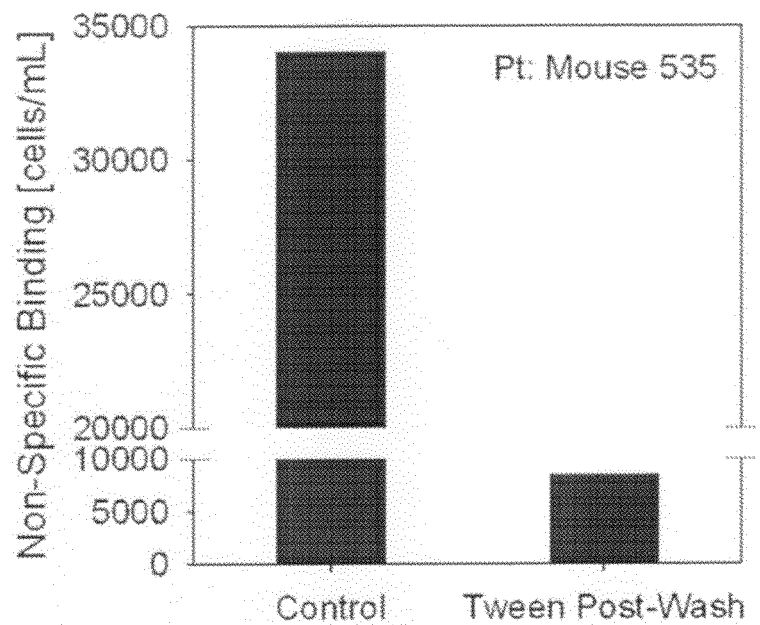
Figure 22B:
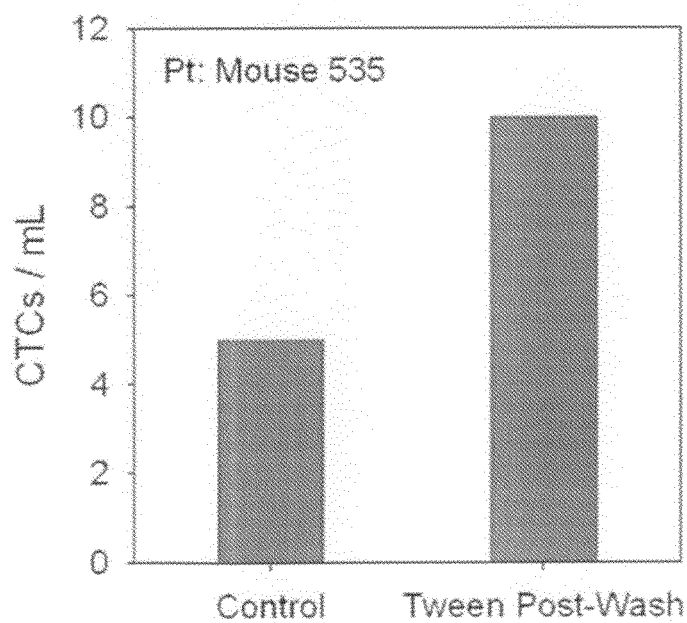

FIG. 22A is a graph of data showing the reduction in non-specific binding in blood from a mouse with pancreatic cancer. FIG. 22B is a graph of data showing an increase in target cell capture in the post-wash chip all in comparison to the control chip.

Figure 23A:
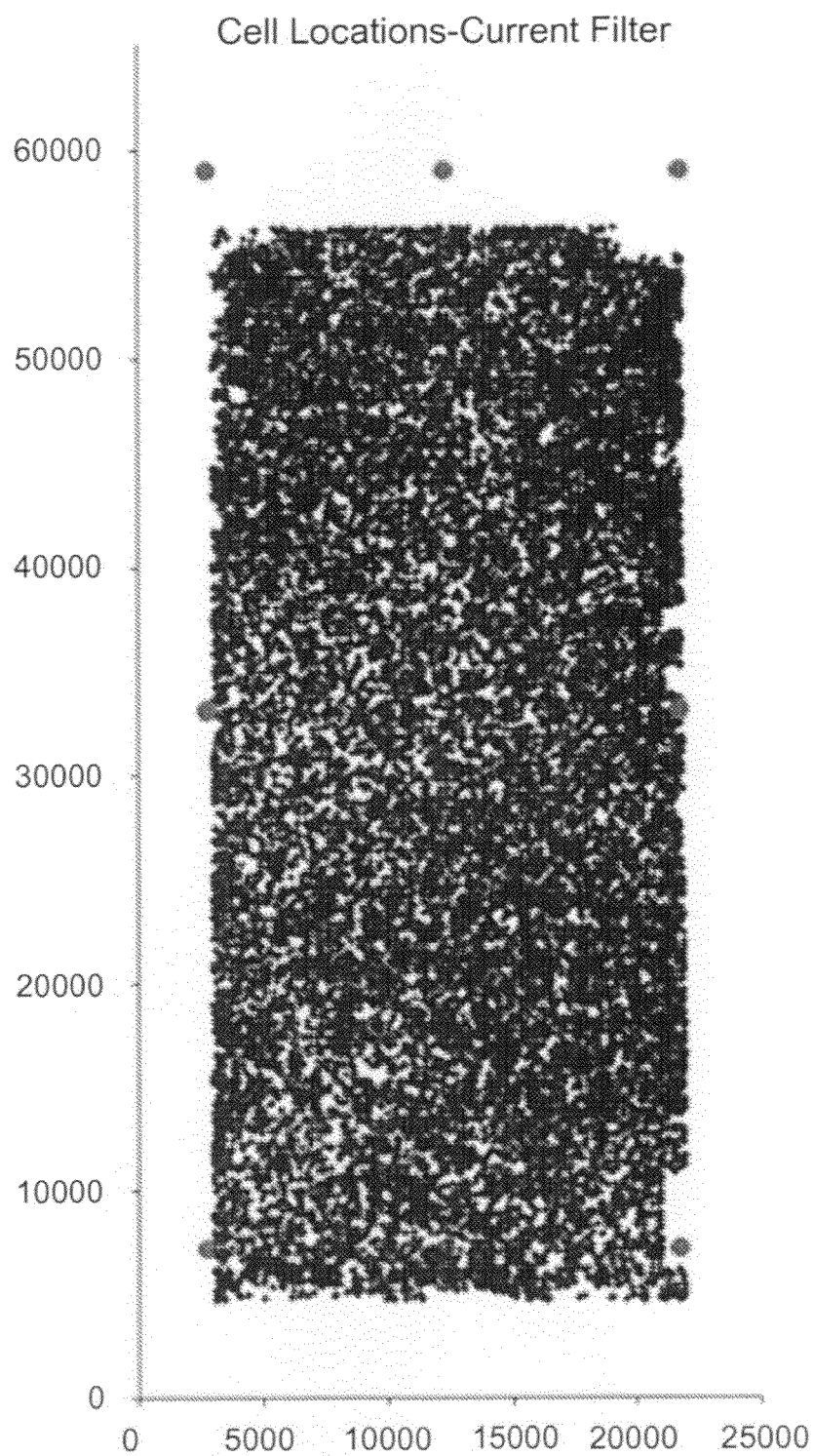
Figure 23B:
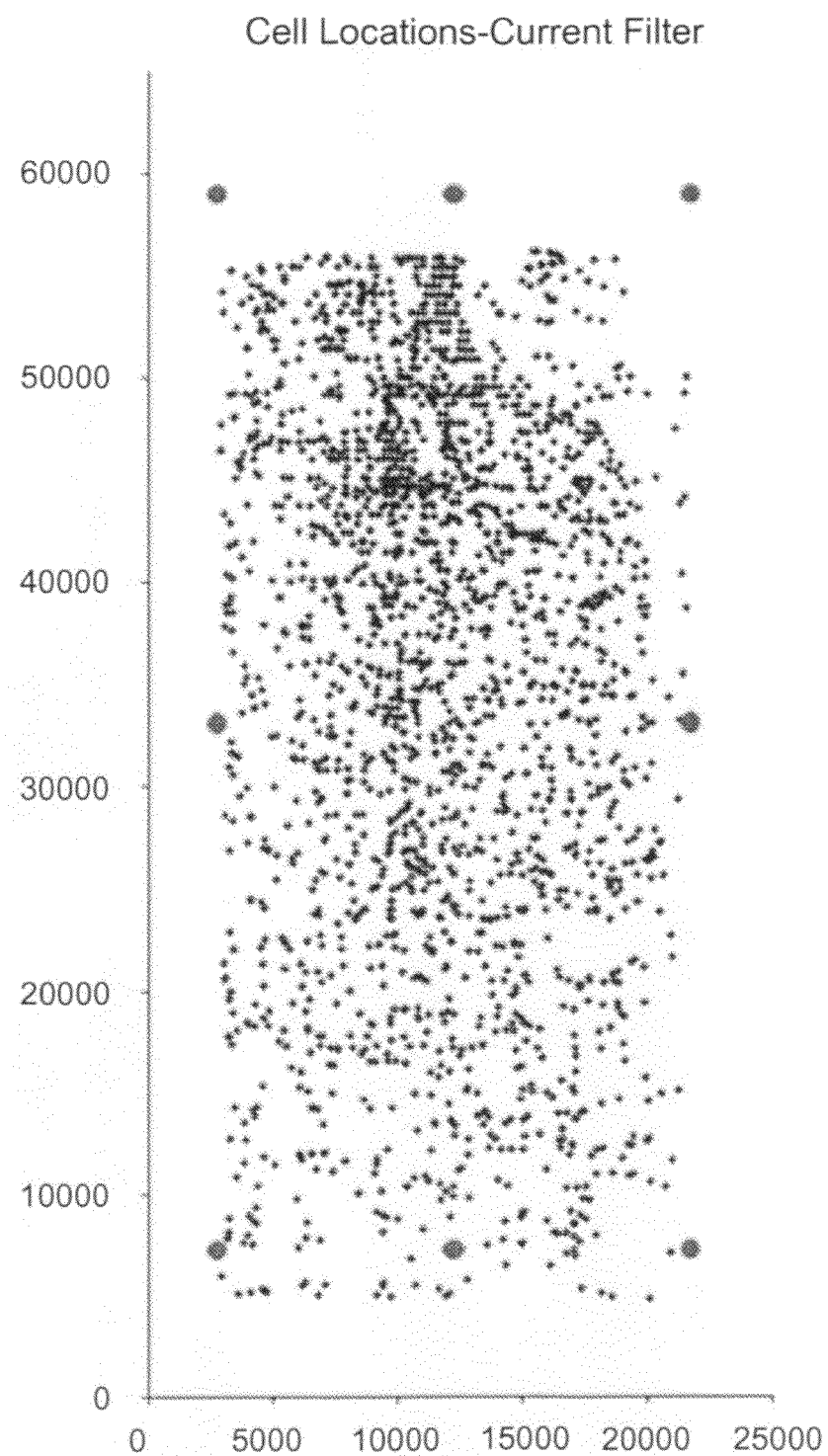
Figure 23C:
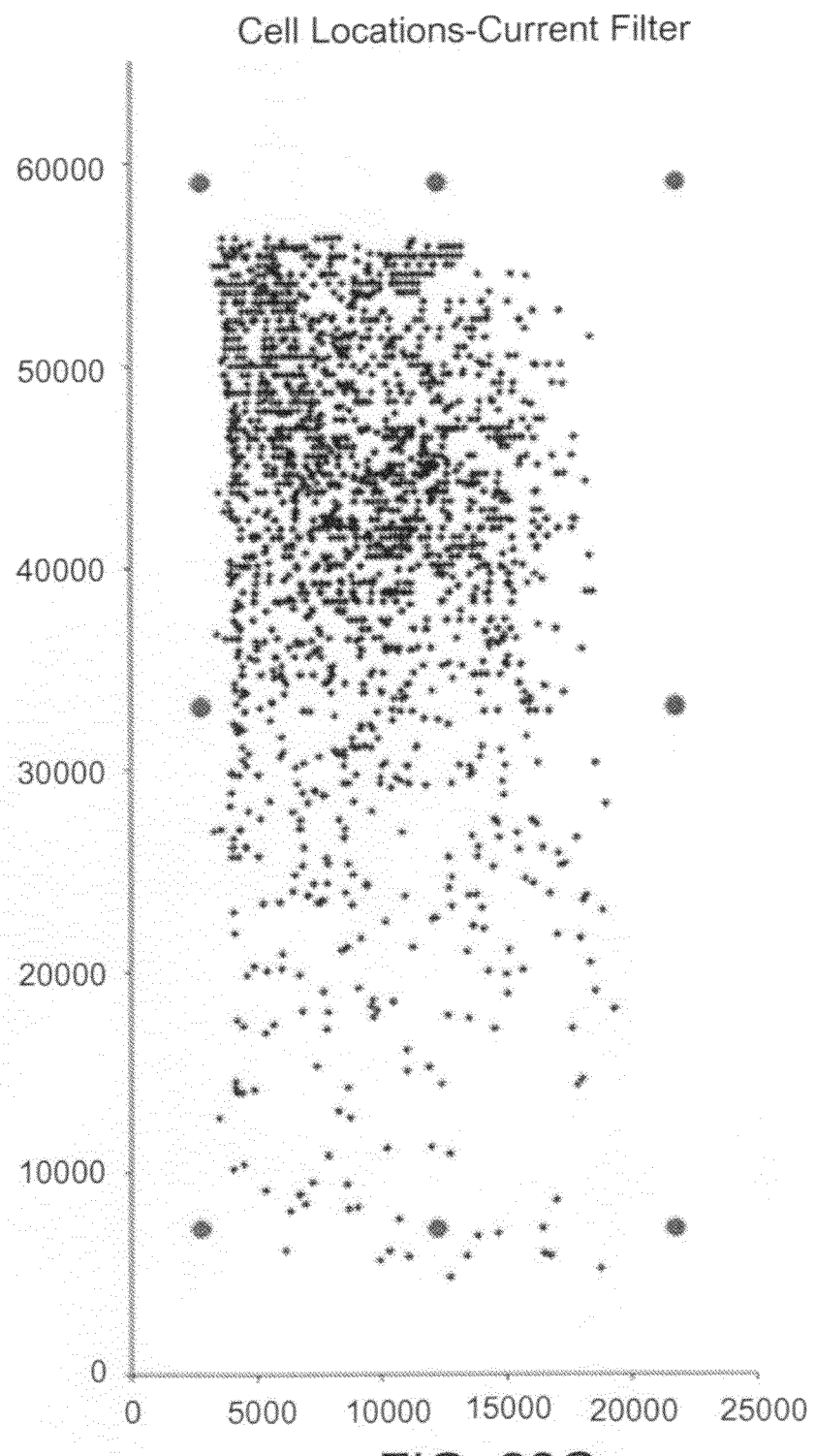

FIGS. 23A-23C are three heat maps showing binding of DAPI positive cells in a microfluidic channel (i.e., each dot represents a DAPI positive bound cell); the top each heat map is the channel inlet. Significantly fewer DAPI positive cells bound to both the first method (EasySep®) and the second method (RosetteSep®).

Figure 24A:
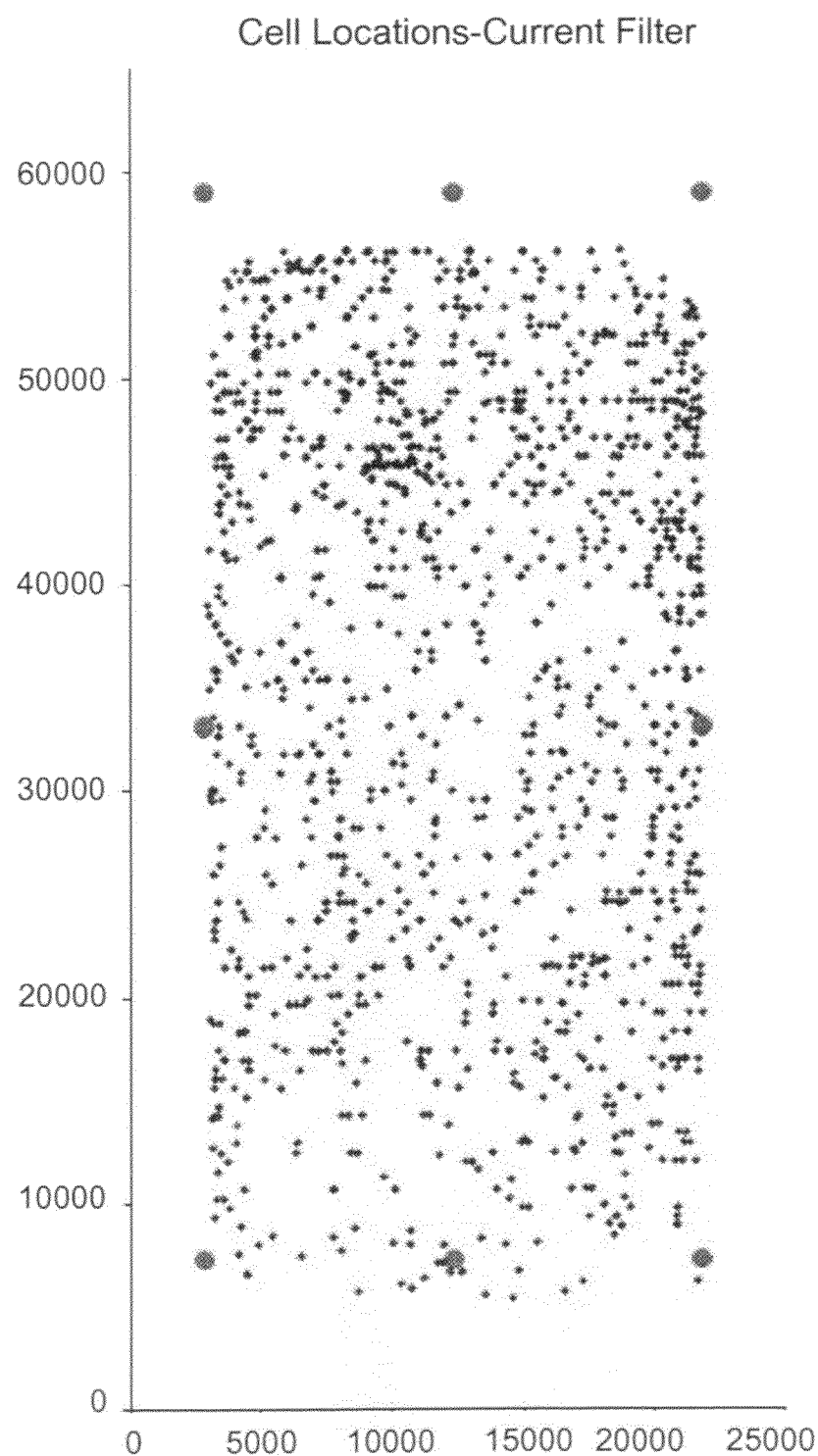
Figure 24B:
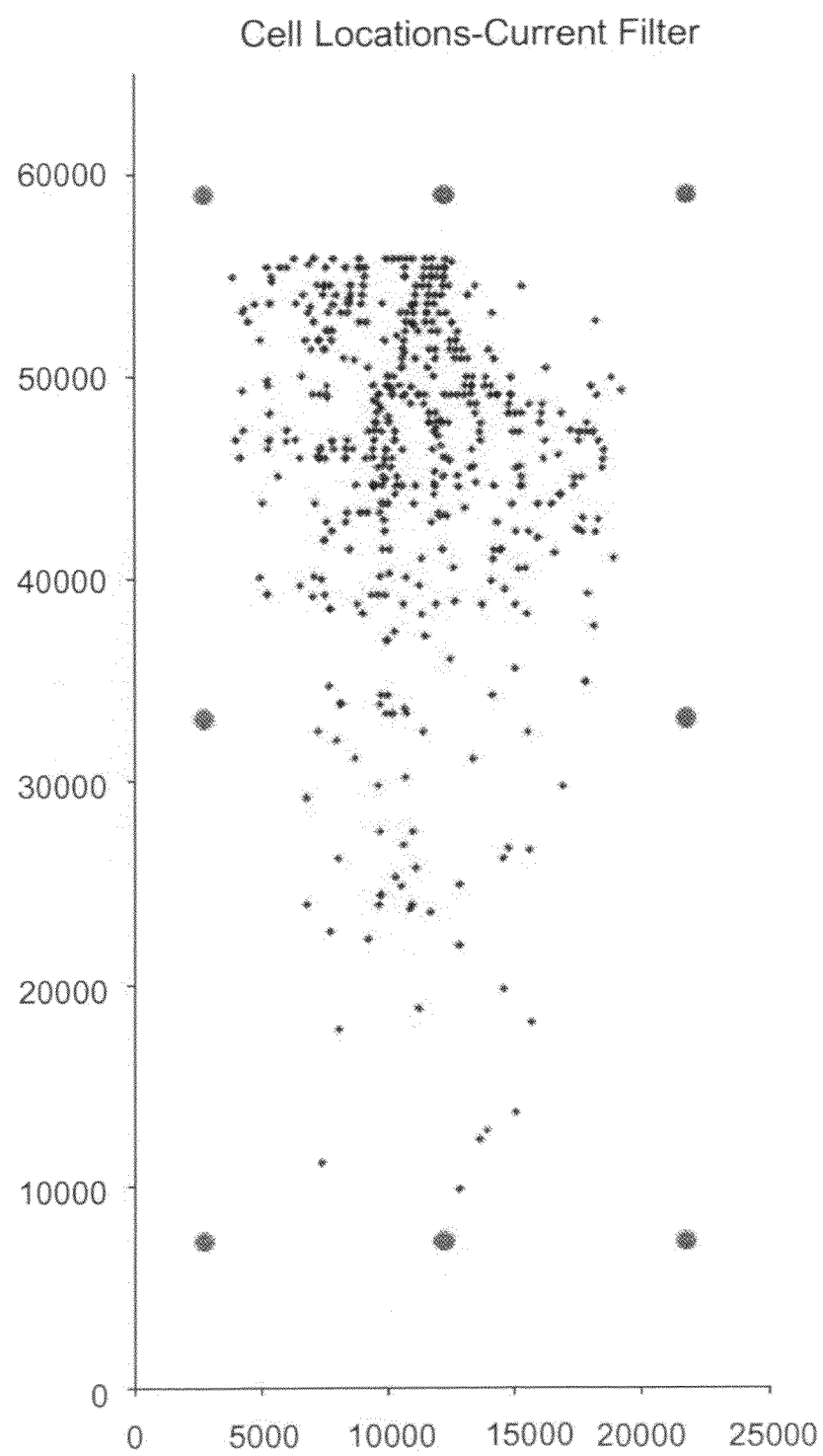
Figure 24C:
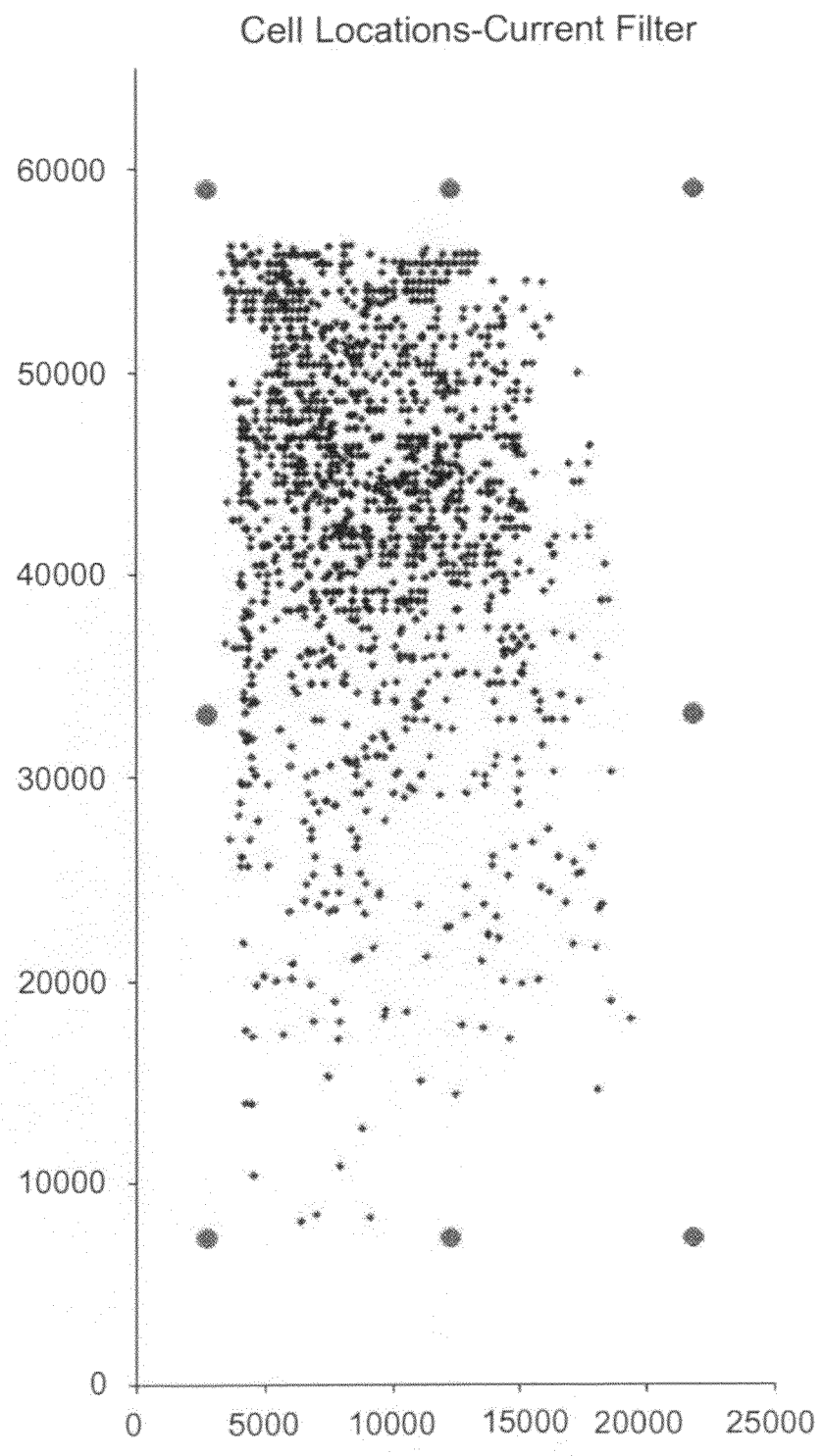

FIGS. 24A-24C are three heat maps for all the target cells found on the microchannels imaged in FIGS. 23A-23C. Each dot in FIGS. 24A-24C represents a CAM5.2 (target CTC) Positive cells.

While the present invention will now be described in detail with reference to the figures, it is done so in connection with the illustrative embodiments and is not limited by the particular embodiments illustrated in the figures as described below.

DETAILED DESCRIPTION

The present disclosure provides methods and devices for the selective capture of analytes, e.g., cells, in a multi-component biological sample, such as the capture of rare cells, e.g., CTCs, from a blood sample, as well as to systems and devices for selective analyte capture.

GENERAL METHODOLOGY

Methods of capturing "rare" analytes, such as CTCs, from a biological sample using surface-bound antibodies can be limited by low expression of corresponding antigens on the surface of a cell. The methods and devices described herein can, in principle, be employed to separate and isolate any rare analyte that can be bound by a selective analyte binding moiety, i.e., a moiety that binds selectively, e.g., preferentially, to the target analyte, e.g., a rare cell, and not to (or at least not to the same extent to) a non-target analyte, e.g., some other type of cell in the sample. The term "rare analyte" as used herein is not limited to "rare cells" that are present in low numbers within a given sample. Instead, the term "rare" as used herein also covers situations in which the cells of interest may be quite abundant within a given sample (e.g., stem cells), but have low surface antigen presentation that would make them untenable for capture in flow based devices based on affinity sorting. Thus, the new amplification methods and systems are universally applicable to any "rare" analyte, e.g., any cell with low surface expression of a specific antigen, regardless of the incidence frequency of the cells.

A rare cell of interest can be, for example, a circulating tumor cell (CTC) of epithelial origin from peripheral blood. Other rare cells include organisms potentially found in peripheral blood (e.g., bacteria, viruses, protists, or fungi), other non-hematopoietic cells not normally found in blood (e.g., endothelial cells or fetal cells), and even cells of hematopoietic origin (e.g., platelets, sickle cell red blood cells, and subpopulations of leukocytes). The analyte binding moiety or moieties employed will depend on the type of cell or cells being targeted.

Specific or selective analyte binding moieties for individual types of analytes are known in the art. Exemplary types of binding moieties include antibodies, antibody fragments (e.g., Fc fragments), oligo- or polypeptides, nucleic acids, cellular receptors, ligands, aptamers, MHC-peptide monomers or oligomers, biotin, avidin, oligonucleotides, coordination complexes, synthetic polymers, and carbohydrates. Analyte binding moieties are each linked to a plurality of other binding agents to form multivalent tagging agents using methods known in the art. For example, biotinylation of antibodies can be accomplished through multiple routes by one skilled in the art, by reacting with the various moieties present, including but not limited to primary amines, sulfhydryl groups, and carboxyl groups. These routes can be either chemical or enzymatic and are typically mediated by a reactive group attached to the binding agent, e.g., biotin. The methods employed will depend on the binding moiety, the binding agent, and the materials used to construct the tagging agent. For example, when isolating CTCs, a useful analyte binding moiety is anti-EpCAM antibody, which is specific for epithelial cells. As described, circulating epithelial cells can provide clinical and diagnostic information relevant to tumors, even those considered clinically localized.

Capture agents that can bind to the binding agents are designed to include a ligand that binds, e.g., binds strongly, to the binding agents. Many ligand/binding agent pairs are known in the art. For example, one well-known ligand-binding agent pair is avidin (e.g., neutravidin or streptavidin) and biotin. Other ligand-binding pairs include histidine—nickel, glutathione S-transferase (GST)—glutathione, maltose binding protein (MBP)—maltose, FITC—anti-FITC, c-myc— tag—anti-c-myc, human influenza hemagglutinin (HA)—anti-HA. The capture agents can be attached to the surfaces of devices using a variety of known methods. Examples of attachment methods include non-specific adsorption to the surface, either of the capture agent or a compound or molecular linker to which the capture agent is attached, or chemical binding, e.g., through self-assembled monolayers or silane chemistry.

When surfaces comprising antibodies specific for an analyte are used as the capture agent, the efficiency of analyte capture naturally depends on the degree to which the analyte consistently includes the corresponding antigen. When the analyte is a cell, an antigen may or may not be consistently or frequently expressed on the surface of a particular analyte cell. For example, CTC capture efficiency decreases as a function of decreasing EpCAM expression. In addition, the statistical probability of capture agent interaction with the target antigen is also limited by the low CTC concentration in biological samples such as blood. Methods of improving the capture efficiency of rare analytes in biological samples, and related microfluidic devices, are disclosed herein. The new methods and devices described herein can enhance the signal to noise ratio and can improve the minimum detectable levels of CTCs in a biological system. The new methods increase or amplify the number and/or the affinity of associative interactions between the cell and a microfluidic device surface to provide signal amplification.

The selective capture of a rare analyte such as a CTC in a biological sample can be enhanced by forming an analyte complex within a biological sample, and then contacting the biological sample with a conjugate capture agent to capture the analyte complex. The analyte complex includes an analyte bound to a multivalent tagging agent. The tagging agent includes an analyte binding moiety (e.g., an antibody specific for the analyte), linked to a cluster of multiple other binding agents, such as biotin. These clustered binding agents in the analyte-tagging agent complex can be selectively bound by a surface-bound capture agent (such as streptavidin) to capture the analyte-tagging agent complex from the biological sample. The associative interaction between the binding agents and the surface-bound conjugate capture agent can be, but need not be, greater than the associative interaction between the analyte binding moiety and the analyte.

In general, a multivalent tagging agent includes an analyte binding moiety, such as a CTC binding moiety (e.g., an anti-EpCAM antibody) and also includes two or more additional binding agents (e.g., 2-10 biotin molecules) that can bind to a capture agent (e.g., streptavidin) and that are all linked to the analyte binding moiety through some molecular linker. Thus, the binding of a rare analyte in a biological sample can be enhanced or amplified by combining the sample with the multivalent tagging agent that selectively binds to an analyte in the sample, thus depositing thousands, tens of thousands, or even a million or more binding agents in clusters on the surface of each analyte in the sample, and then contacting the sample to a surface configured with capture agents whose ligands selectively bind to one or more of the clustered binding agents that are part of the multivalent tagging agent (bound to the analyte by their analyte binding moiety).

The multivalent tagging agents can be bound to the analytes in different ways. For example, the first part of the tagging agent, the analyte binding moiety, can first be bound to the analytes in a sample, and then the second part of the tagging agent, the binding agents, can be linked to the analyte binding moieties using any of various molecular linking systems, such as tyramide signal amplification using horse radish peroxidase (HRP) bound to the analyte binding moiety. Alternatively, other linking systems such as dendrimer systems and rolling circle amplification can be used to link the binding agents to the analyte binding moieties.

Figure 1:
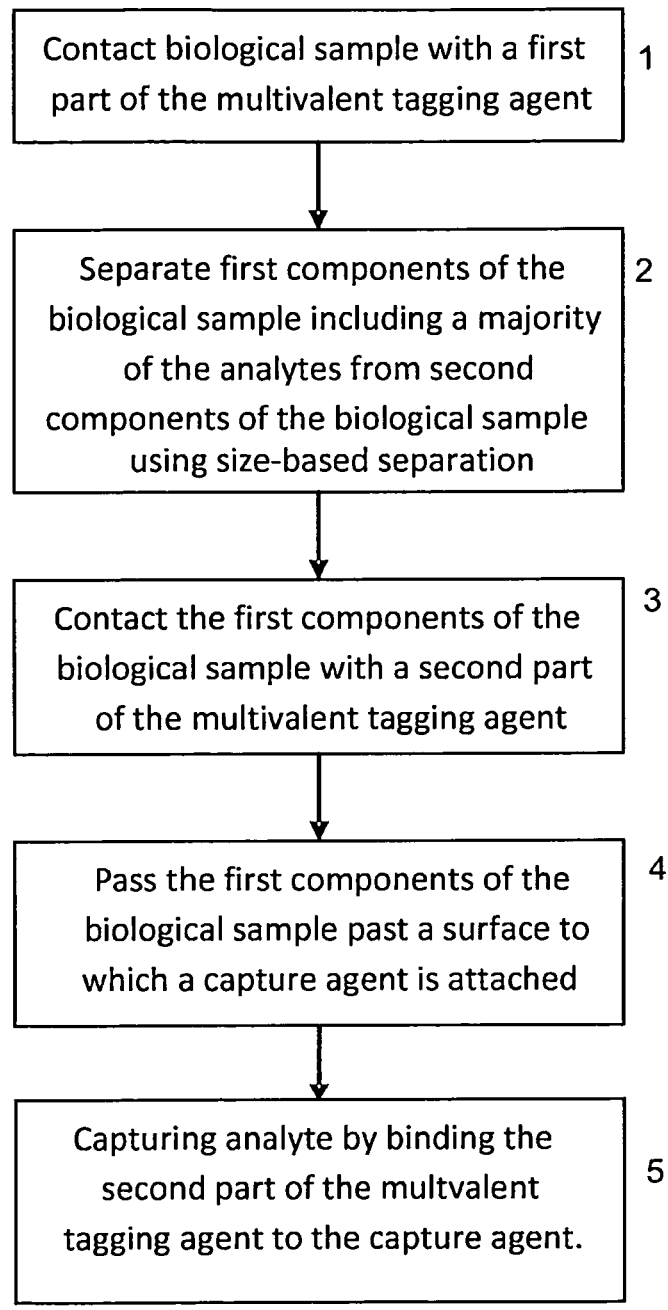
FIG. 1 is a schematic block diagram that illustrates a method of selectively capturing analytes from a biological sample.

FIG. 1 shows a method of selectively capturing analytes from a biological sample. The new methods of selectively capturing analytes from a biological sample include contacting the biological sample with a multivalent selective tagging agent that provides the basis for formation of an analyte-binding agent complex (step 1). For example, an anti-EpCAM-HRP complex (which includes the analyte binding moiety, which is the first part of the tagging agent) can be added to a whole blood sample containing small numbers of CTCs (e.g., less than about $10^{-6}$/mL in the biological sample) with low EpCAM expression. Size-based separation techniques can then be used to separate first components (e.g., white blood cells and CTCs with attached anti-EpCAM-HRP complex) of the biological sample from second components (e.g., red blood cells, platelets, and plasma) of the biological sample (step 2). The first components (e.g., white blood cells and CTCs with attached anti-EpCAM-HRP complex) of the biological sample can be combined with a second part of the multivalent selective tagging agent (e.g., the binding agent, e.g., in the form of a tyramide-biotin complex) (step 3).

Flow of the first components of the biological sample can then be directed past a surface to which a conjugate capture agent (e.g., avidin, neutravidin, or streptavidin) is attached (step 4). For example, the conjugate capture agent can be attached to surfaces of microfluidic chips including surfaces of posts and/or V-shaped grooves that are designed to control sample flow. In some embodiments, the capture agent can be attached to surfaces of beads or particles, e.g., magnetic beads, or other solid-state capture devices. Thereafter, binding between the second part of the multivalent selective tagging agent (the binding agent) and the ligand of the capture agent can capture the analyte of interest on the surface to which the conjugate capture agent is attached (step 5).

These approaches are effective for low levels of analytes. In addition, these methods are effective with low levels of peroxidase. The use of lower levels of peroxidase compared to other approaches can significantly reduce the formation of radicals in white blood cells downstream in the system. This is important, because the presence of too many radicals can activate the white blood cells and cause non-specific retention of these cells in the microfluidic devices. The key is to amplify cells of interest without inducing collateral damage to white blood cells in the sample.

Figure 2A:
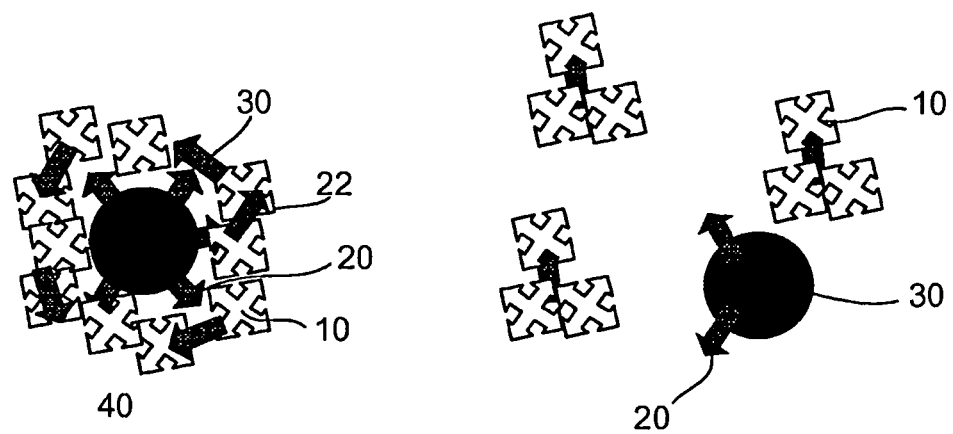
FIGS. 2A-2C are schematic diagrams showing the associative interaction between a cell analyte, a biotinylated antibody, a multivalent biotin species and a biotin-binding conjugate.
Figure 2B:
Figure 2C:
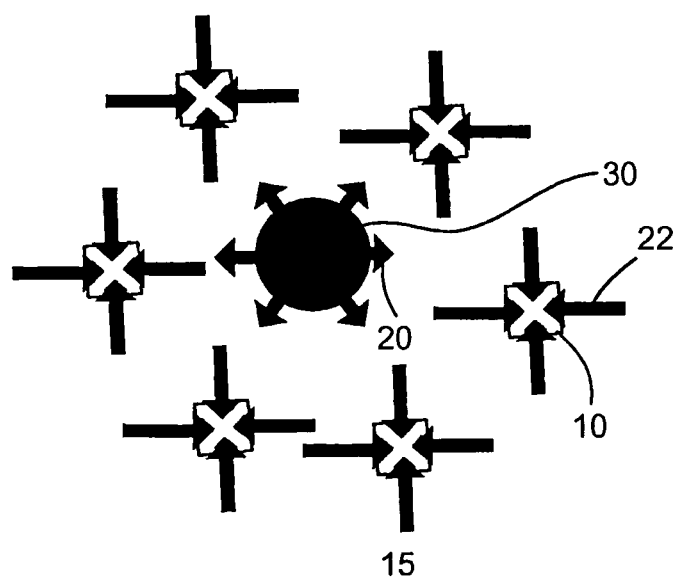

In one example, the analyte is a cell in a biological sample and the analyte binding agent is an antibody that binds specifically to an antigen expressed on the surface of the cell. The antibody can be modified to bind to a conjugate capture agent, for example by biotinylation. In some examples, the surface-bound capture agent can comprise the same molecule as the analyte binding moiety. As shown in FIGS. 2A-2C, a cell complex 40 can include a CTC 30 bound to a biotinylated antibody 20 and multiple biotin-binding conjugates 10 and biotin 22. For example, by incubating CTCs 30 with biotinylated EpCAM antibody 20, each receptor becomes tagged with multiple biotins (e.g., 2-10/antibody). This effect could be further amplified by including a multivalent biotin-binding conjugate 10 (e.g., streptavidin) to load additional biotin in a specific manner. The cell complex 40 can be associatively bound to a surface-bound biotin-binding conjugate (e.g., the capture agent can be streptavidin) to capture the cell complex 40. By capturing the CTCs within the cell complex 40 instead of capturing the CTCs 30 with a surface-bound antibody (e.g., surface bound EpCAM), the CTCs are captured using one or more avidin-biotin interactions instead of the corresponding antibody-antigen interaction (e.g., EpCAM-CTC interaction).

The rate of CTC cell capture can be amplified by formation of a cell complex having a greater binding affinity for the conjugate cell-binding agent than the antibody would have for the CTC. This provides increased capture affinity to each CTC, because the binding affinity of an individual biotin-binding capture pair is significantly higher than the corresponding antibody-antigen interaction (e.g., EpCAM-CTC interaction) (avidin-biotin $Kd=10^{-15}$, antibody-antigen $Kd=10^{-9}$).

The amount of biotinylated antibody, free multivalent biotin-containing entities, and biotin-binding conjugate (e.g., streptavidin) added to a biological sample can be selected to form the desired cell complex within the biological sample. For example, a blood sample containing CTCs can be incubated with biotinylated EpCAM antibody, free multivalent biotin containing entities and streptavidin (or another biotin-binding conjugate) for a suitable period of time (e.g., 20-30 minutes) to form the CTC cell complex comprising the CTC bound to the biotinylated EpCAM antibody, biotin, and streptavidin. For example, as shown in FIG. 2A, the CTC cell complex 40 includes a biotinylated EpCAM antibody that is attached directly to the cell via antibody-antigen interaction to participate in networking with additional biotinylated antibody via streptavidin crosslinks resulting in increased overall biotin loading, and making the CTC complex 40 more conducive to capture with streptavidin-modified surfaces.

In contrast, FIGS. 2B and 2C show instances where the CTC cell complex does not form in the biological sample. FIG. 2B shows the formation of biotin-streptavidin complexes in the biological solution as a result of adding too much streptavidin to the biological sample comprising the CTC 30 bound to a biotinylated EpCAM antibody 20 (no amplification). FIG. 2C shows the formation of complexes in the biological solution between the biotinylated antibody and streptavidin as a result of adding too much biotinylated antibody to the biological sample (no amplification).

Amplification Methodology

It has been discovered that initially adding a two-part multivalent selective tagging agent that includes as the first part an analyte binding moiety, such as, for example, an anti-EpCAM-HRP complex, and as a second part, a plurality of another binding agent, such as biotin, provides the basis for subsequent formation of an analyte complex, which can provide unexpectedly increased selective capture compared to direct biotin addition using biotinylated-anti-EpCAM antibodies. As discussed in more detail below, it is thought that multivalent tagging agents that include analyte binding moieties such as the anti-EpCAM-HRP linked to multiple biotin binding agents cause a clustering of the biotin once the biotin is attached or linked to the analyte binding moiety, which may influence the increased capture observed.

Figure 3:
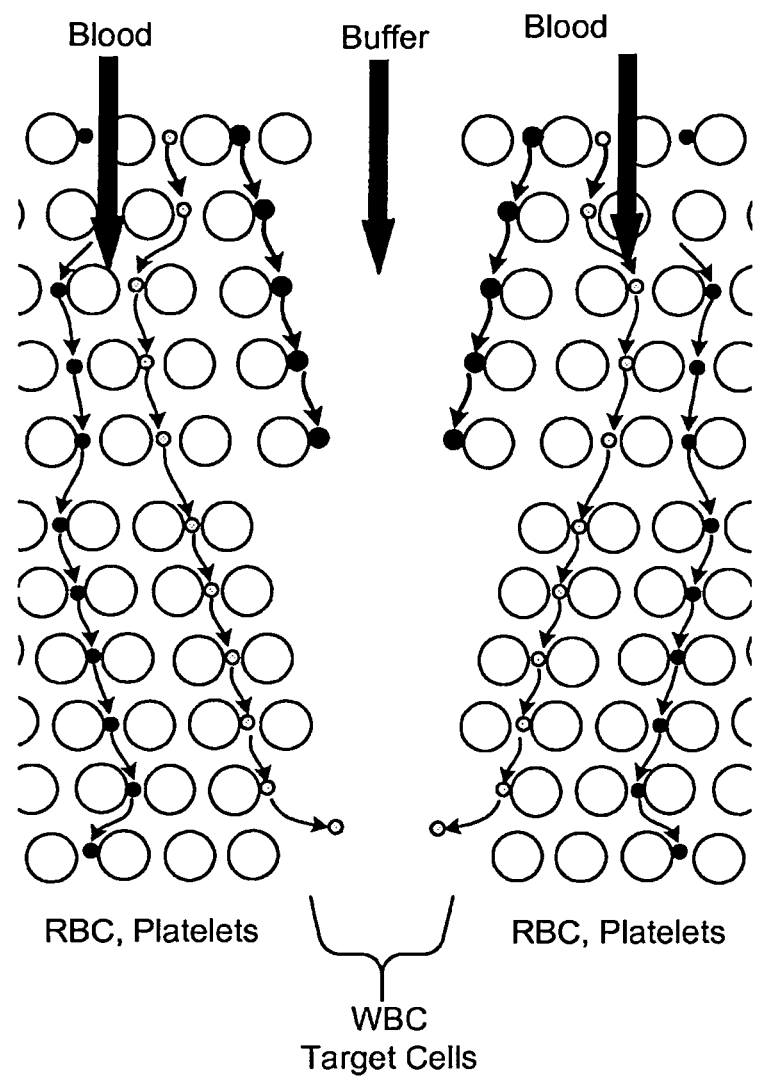
FIG. 3 is a schematic diagram of a microfluidic device for size-based separation of components.

Referring to FIG. 3, sized-based separation can be performed using arrays of obstacles, e.g., posts or walls, which are designed and arranged to cause deterministic lateral displacement of components of fluids base on the size of the components. The obstacles are arranged to provide a network of gaps such that a fluid passing through a gap is divided unequally into subsequent gaps. The obstacles and gaps can be arranged as shown in FIG. 3 to cause particles having a hydrodynamic size larger than a critical size migrate diagonally to a bypass channel while particles having a hydrodynamic size smaller than the critical size follow the flow in a different direction. Such size-based separation devices are discussed in more detail in U.S. Pat. Pub. No. US 2007-0026381, which is incorporated herein by reference in its entirety. Other size-based separation methods and devices are discussed in more detail in U.S. Pat. Pub. No. US 2007-0160503, which is incorporated herein by reference in its entirety.

For example, an anti-EpCAM-HRP complex can be added to a whole blood sample containing small numbers of CTCs (e.g., less than about $10^{-6}$/mL in the biological sample) with low EpCAM expression. Size-based separation techniques can be used to separate white blood cells and CTCs with attached anti-EpCAM-HRP complexes from red blood cells, platelets, and plasma. Anti-EpCAM-HRP complexes not attached to CTCs are small and will tend to be directed in the same flow stream as the red blood cells, platelets, and plasma. This separation can eliminate unbound Ab-HRP complexes and red blood cells/platelets/plasma in a 1-step gentle microfluidic process with greater than 99% retention of rare cells in a background of white blood cells.

Because unattached complexes of the first part of the multivalent tagging agent are separated from the target cells, this allows relatively high levels of the first part of the multivalent tagging agent to be used to increase the likelihood that all target cells are tagged without an associated increase in the likelihood that the scenario shown in FIG. 2C will occur. In some embodiments, size-based separation can be performed before the addition of the first part of the multivalent tagging agent, i.e., the selective analyte binding moiety. This may undesirably increase the likelihood of interference in the process due to excess unattached complexes of the selective analyte binding moiety.

After the sized-based separation, a second part of the multivalent tagging agent, the binding agent, such as in the form or a tyramide-biotin complex, can be mixed with the white blood cells and CTCs with attached anti-EpCAM-HRP complexes using standard tyramide signal amplification (TSA) techniques (see, e.g., U.S. Pat. No. 5,731,158, which is incorporated herein by reference in its entirety, including the description of TSA). Removal of the unbound Ab-HRP complexes and red blood cells/platelets/plasma through size-based separation, as described above, can enable simple addition of the tyramide-biotin complex to cause site-directed HRP-mediated amplification of target cells. The reaction can be quenched by adding bovine serum albumin. As these are additive steps, there is typically little to no loss of the target rare cells. This can be a significant advantage of the present techniques relative to techniques that require, for example, washing steps during which target rare cells can be lost.

Figure 4A:
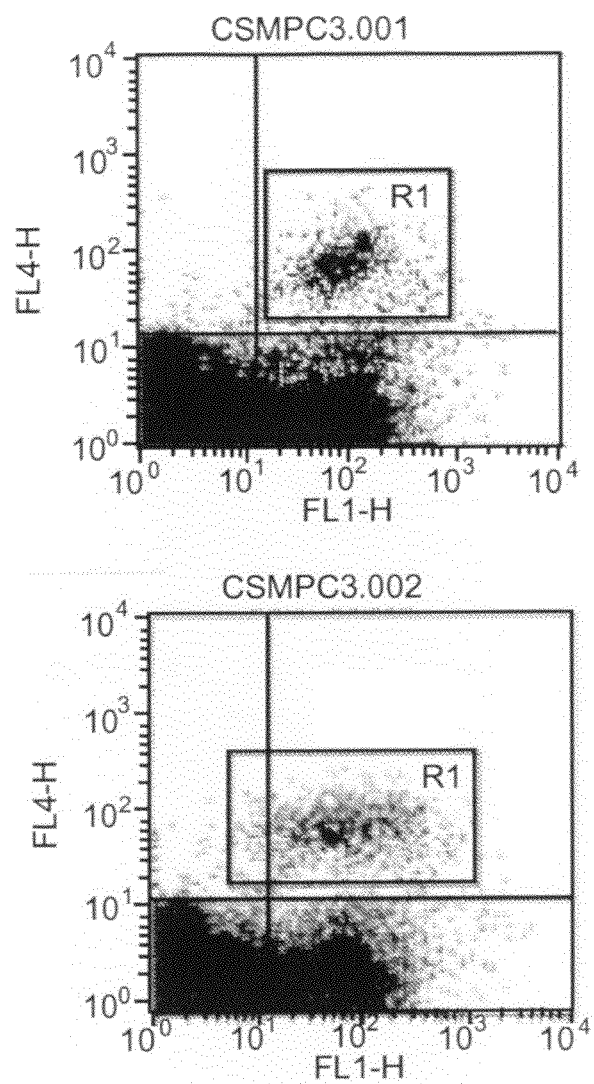
Figure 4B:
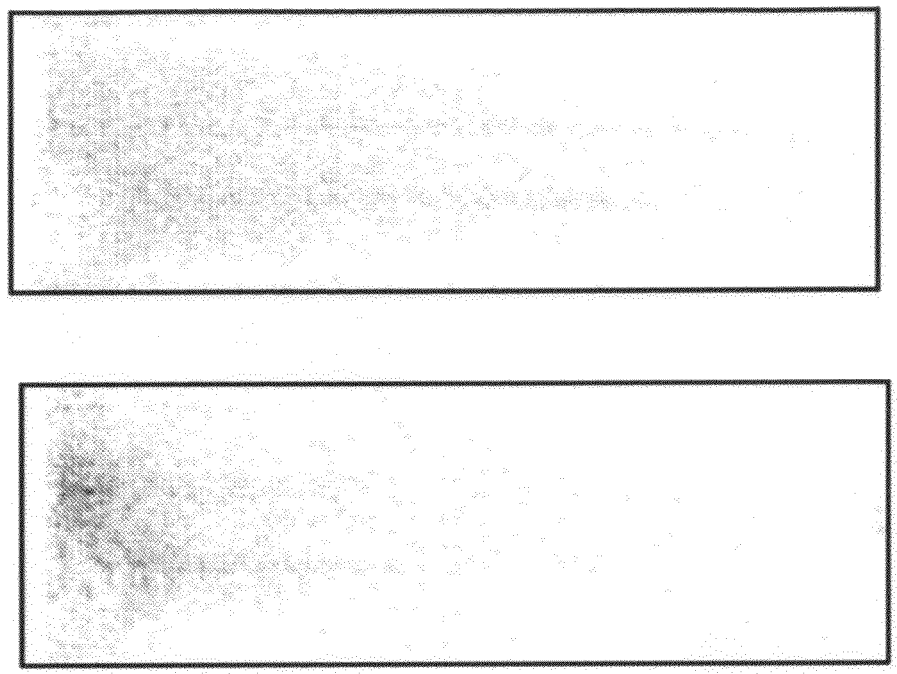

FIGS. 4A-4C present evidence that suggests that the enhanced capture of the amplified target cells is not solely due to the extent of amplification/biotinylation. This is evidenced by the fact that populations of target cells with similar levels of amplification/biotinylation exhibited distinctly different capture behavior. FIG. 4A shows the inflow of cells into a microfluidic device with the biotinylation indicated. Both the control sample on the left and the test sample on the right included 5000 tumor cells/ml. The control sample was biotinylated using the addition of anti-EpCAM-biotin complexes. The test sample was biotinylated using the addition of anti-EpCAM-HRP complexes and the subsequent addition of tyramide-biotin complexes to form multivalent tagging agents in situ. The mean biotinylation of the control sample was 120 relative fluorescence units (RFU) and the mean biotinylation of the test sample was 111 RFU. Thus, FIG. 4A demonstrates that there was no significant difference in terms of amplification, and thus no apparent benefit of the use of the multivalent tagging agent.

However, capture "heat maps" of amplified cells (see FIG. 4B) exhibited markedly better than predicted (based on the flow results shown in FIG. 4A) capture on the microfluidic chip, as indicated by the much higher density of events (i.e., cells) captured near the inlet (on the left side of the "map") and shorter overall penetration into the chip before being captured. This is confirmed by examining capture histograms which clearly indicate an inlet-biased capture with a very steep decay profile (see FIG. 4C). As shown, on the left side of FIG. 4C, the capture histogram shows a broad decay profile, while the histogram on the right side of FIG. 4C, which corresponds to the test sample shows a much steeper decay profile, indicating most of the cells were captured very close to the inlet.

One hypothesis consistent with these observations is that the process of amplification results in a clustered deposition of biotin molecules (as shown in FIG. 4D). A uniform distribution of biotin would translate to a capture probability similar across the cell surface. In the clustered case, there are local areas of potential interaction with a significantly higher capture probability than the average. As the threshold for the minimum required interaction for cell capture is approached, the clustered event maintains areas of non-zero probability of capture even though the average probability is below the required amount. Conversely, the Uniform event fails to capture once it crosses this threshold.

The sample can then be mixed with, for example incomplete Dulbecco's Phosphate Buffered Saline (iDPBS) (without calcium or magnesium) and 1% bovine serum albumin to resuspend the cells. Flow of the first components of the biological sample can then be directed past a surface to which a conjugate capture agent (e.g., avidin, neutravidin, or streptavidin) is attached. For example, the conjugate capture agent can be attached to surfaces of microfluidics chip including posts and/or V-shaped grooves to control sample flow with the conjugate capture agent attached to surfaces of the chip. In some embodiments, the conjugate capture agent can be attached to surfaces of magnetic beads or other solid-state capture devices. Binding between the second multivalent selective binding agent and the conjugate capture agent can capture the analyte of interest on the surface to which the conjugate capture agent is attached.

The tyramide system is one embodiment of the describe amplification methodology that enables the deposition of clustered binding agents, such as biotin molecules, in a manner that ensures the binding agents are accessible for cell capture. In another embodiment, one could pre-form the biotin cluster using dendrimers with a number of arms (n=4, 6, 8, 10, 15, 20, 25, 30, 35, 50, 60, 70, 80, 90, or 100, ideally between about 8 and about 80, but higher would work also so long as the degree of substitution and the linker length from the core to the biotin are optimized to prevent steric hindrance). This cluster of binding agents attached to the dendrimer can then be attached to the analyte binding moiety (e.g., an antibody that provides immunospecificity) in a variety of ways: directly if it is pre-conjugated, or added later using an avidin sandwiching approach. Alternatively, it could be linked to the antibody through an in situ chemical or photochemical reaction or other specific hybridization/conjugation.

In general, dendrimers are repeatedly branched, typically symmetric around a core, and often adopt a spherical three-dimensional morphology. Dendrimers have a strong potential for the methods described herein, because their structure provides a multivalent system, where one dendrimer molecule has dozens to hundreds of possible sites to which the binding agents can be couple to the analyte binding moiety.

Although the biotin/avidin ligand binding pair is a strong choice due to excellent sensitivity and specificity, the amplification capture scheme is not limited to biotin/avidin. For example, an analyte binding moiety, such as an antibody, could be modified to carry one or more DNA probes to serve as primers for Rolling Circle Amplification (RCA). Target analyte cells tagged with the modified antibody are then exposed to a circular DNA template in the presence of DNA polymerase. Thousands of copies of the template are generated, all linked or tethered to the original DNA target. The amplified cells are then amenable to capture on devices functionalized with the complementary sequence to the template.

In general, RCA is a process of unidirectional nucleic acid replication that can rapidly synthesize multiple copies of circular molecules of DNA or RNA, such as plasmids, the genomes of bacteriophages, and the circular RNA genome of viroids. Rolling circle replication has been successfully used for amplification of DNA from very small amounts of starting material and to detect proteins (see, e.g., Cho et al., J. Am. Chem. Soc., 127:2022-2023 (2005) and Nallur et al., Biomedical Microdevices, 5:115-123 (2003), which are both incorporated herein by reference. To detect an analyte, e.g., an antigen expressed on the surface of a cell, an oligonucleotide primer is attached covalently to an antibody that specifically binds to the antigen, allowing analytes to be detected with higher sensitivity than conventional enzyme immunoassays. Nucleic acid synthesized through this amplification step can hybridize to another primer attached covalently to the binding agent, e.g., another antibody, and the process can be repeated to link many hundreds, thousands, tens of thousands, or more binding agents to analyte binding moieties.

Cell Capture Devices

The CTC cell complex can be captured from the biological sample within a microfluidic channel. The channel can include a surface configured to capture the CTC cell complex. The channel can be formed within a microfluidic device configured to capture CTCs (a "CTC-chip") from peripheral whole blood samples, preferably mediated by the interaction of a CTC complex with a capture agent attached to a surface of the channel. For example, the channel can include posts coated with capture agents that comprise a biotin-binding conjugate agent and are arranged to isolate CTCs in high numbers from whole blood samples within the channel. Such a channel can be used to capture CTCs from blood samples from patients, and is useful both in cancer biology research and clinical cancer management, including the detection, diagnosis, and monitoring of cancer. The exact device geometry will be determined based on the assay.

Figure 5A:
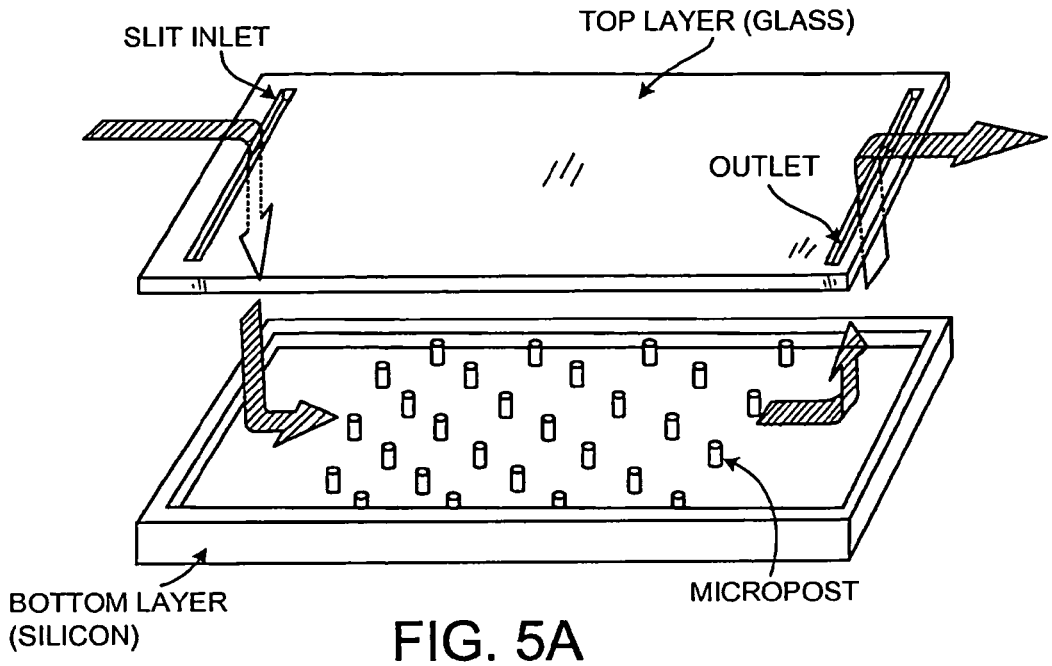
FIG. 5A is an exploded perspective view that shows an example of a microfluidic device including a microfluidic channel for capturing an analyte from a fluid sample.
Figure 5B:
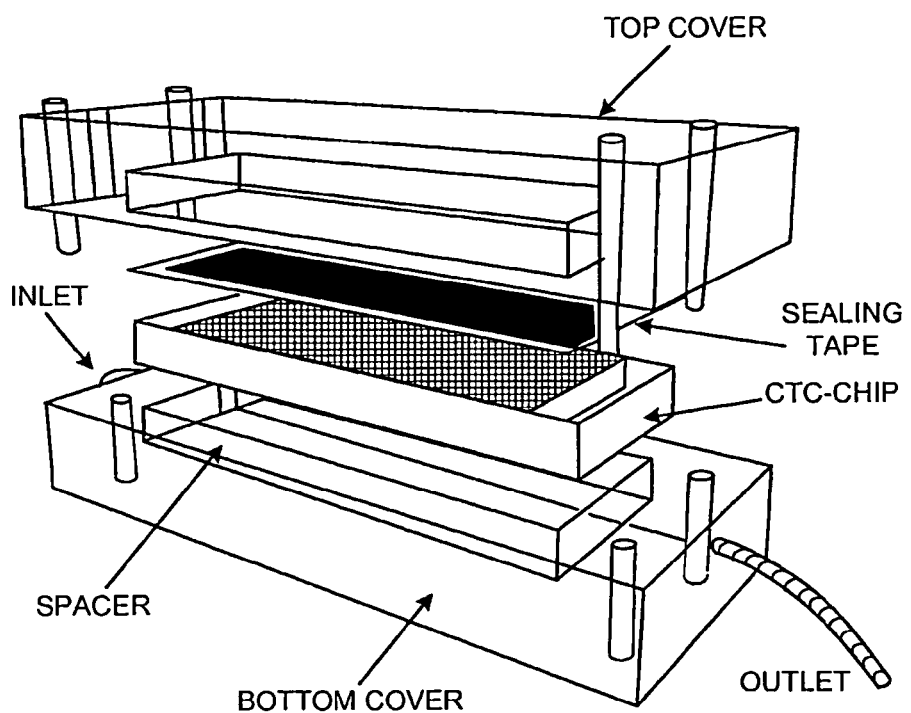
FIG. 5B is an exploded perspective view that shows a device comprising the microfluidic channel in FIG. 5A.
Figure 5C:
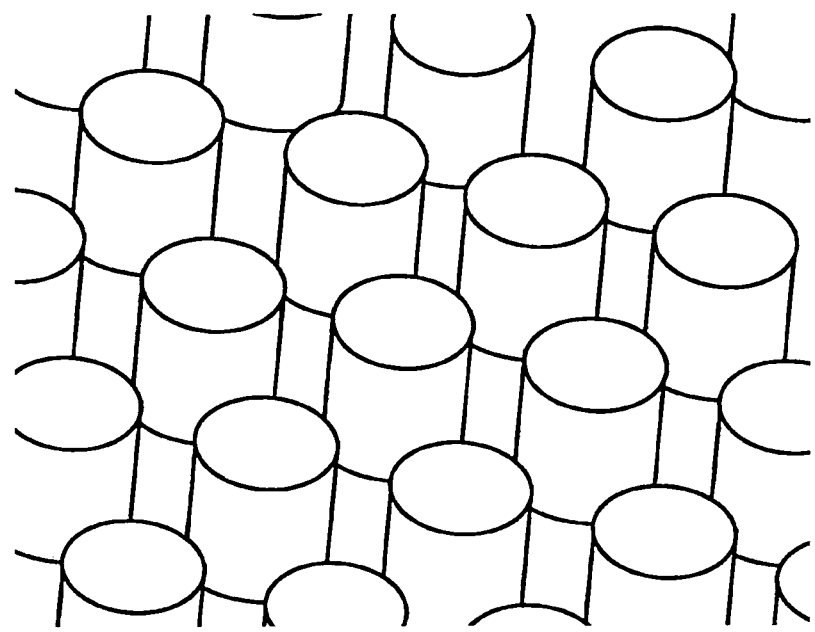
FIG. 5C is a micrograph showing an array of posts formed within a microfluidic channel.

An example of a microfluidic device is shown in FIG. 5A, including a fluid flow channel providing fluid communication between an inlet and an outlet. The channel includes at least one surface configured to bind the CTC cell complex. For example, the surface can include a biotin-binding conjugate bound to the surface. The surface can be formed on one or more posts within the channel configured to capture the CTC cell complex in the biological fluid sample within the channel. The channel shown in FIG. 5A can be included in combination with other components to provide a system for isolating rare analytes from a biological sample. FIG. 5B is a point-of-care device for analyzing blood samples, with the device comprising a microfluidic chip sealed within the manifold. FIG. 5C is a scanning electron micrograph (SEM) image of an array of microposts etched in a silicon surface forming the bottom of the channel shown in FIG. 5A. An example of a useful CTC-chip contains an array of 78,000 microposts within a 970 $mm^2$ surface. The volume of the channel or the region having the binding agents may also be selected depending on the volume of the blood sample being employed. The volume of the channel (defined as that portion through which cells may pass) can be larger than the size of the sample.

Figure 5D:
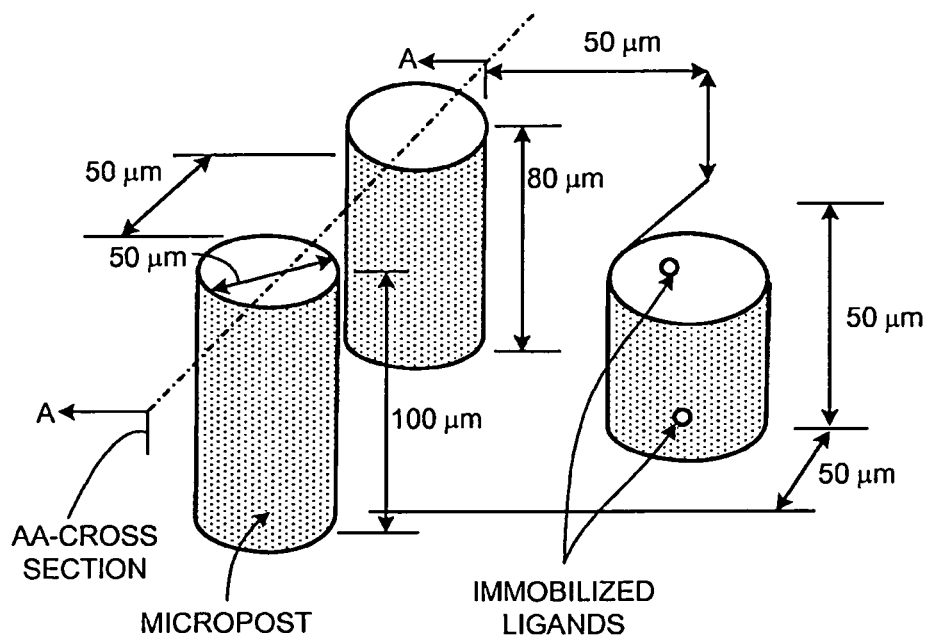
FIG. 5D is a schematic that shows three adjacent posts having different heights within an array of posts in a channel.

Posts of different heights within a microchannel are shown in FIG. 5D. In one example, posts are etched on a surface area of 2 cm×7 cm on a substrate with overall dimensions of 2.5 cm×7.5 cm. A rim of 2 mm can be left around the substrate for bonding to the top surface to create a closed chamber. The posts can have a diameter of 50 µm with a variable height (e.g., 50, 80 and 100 µm). Obstacles can be arranged in a two-dimensional array of rows with a 100 µm distance from center-to-center. This arrangement provides 50 µm openings for cells to flow between the obstacles without being mechanically squeezed or damaged. The obstacles in one row are desirably shifted, e.g., 50 µm with respect to the adjacent rows. This alternating pattern can be repeated throughout the design to ensure increased collision frequency between cells and obstacles. The diameter, width, or length of the obstacles can be at least 5, 10, 25, 50, 75, 100, or 250 µm and at most 500, 250, 100, 75, 50, 25, or 10 µm. The spacing between obstacles can be at least 10, 25, 50, 75, 100, 250, 500, or 750 µm and at most 1000, 750, 500, 250, 100, 75, 50, or 25 µm.

FIG. 2E is a top view of a fluid flow channel with three hemispherical posts oriented with a substantially flat surface positioned substantially perpendicular to the direction of sample fluid flow through the channel (including a plurality of cells within the sample). FIG. 2F is a top view of a fluid flow channel with a lattice of semi-cylindrical posts within the channel. The flat face of the semi-cylindrical post faces towards the flow and increases residence time and increases the probability of capture. FIG. 2G shows fluid flow lines of a sample around the lattice of semi-cylindrical posts shown in FIG. 2F. Adhesion of the cells or cell complexes within the fluid sample can be increased along the flat surface of each hemispherical post due to formation of a stagnation zone in the center of the flat surface, thereby providing a stagnant flow condition increasing residence time and increasing the efficiency of chemical interactions with the binding surface. In general, the surface can be an outer surface of a hemispherical post within the channel, a portion of the surface being oriented substantially perpendicular to a direction of fluid flow of the biological sample within the channel. The post can extend completely or partially across the channel.

One or more surfaces of the microfluidic channel can be configured to direct fluid flow and/or analytes within a fluid passing through the microfluidic channel. For example, the surface of a channel can be rough or smooth. The channel can include a roughened surface having a periodic amplitude and/or frequency that is of a size comparable with a desired analyte. In particular, the channel can be defined by a wall with an undulating or "saw-tooth"-shaped surface positioned opposite the base of one or more posts within the channel. The saw-tooth shaped surface can have a height and frequency on the order of about 1-100 micrometers, and can be positioned directly opposite one or more posts extending only partially across the surface.

The rate and pressure of fluid flow, as well as the channel dimensions, can be selected to provide a desired rate of binding to the surface of the channel. The fluid flow velocity can also be selected to provide a desired shear stress to analytes bound to the surface of the channel. At least two variables can be manipulated to control the shear stress applied to the channel: the cross sectional area of the chamber and the fluid pressure applied to the chamber. Other factors can be manipulated to control the amount of shear stress necessary to allow binding of desired analytes and to prevent binding of undesired analytes, e.g., the binding moiety employed and the density of the binding moiety in the channel. Pumps that produce suitable shear forces in combination with channels of the invention preferably produce a unidirectional shear stress, i.e., there is no reversal of direction of flow, and/or substantially constant shear stress. Either unidirectional or substantially constant shear stress can be maintained only during the time in which a sample is passed through a channel. The flow rate will typically be between 0.1 mL to 30 mL/hr. Dilution of blood can be employed at high flow rates, e.g., above 10 mL/hr.

Figure 6A:
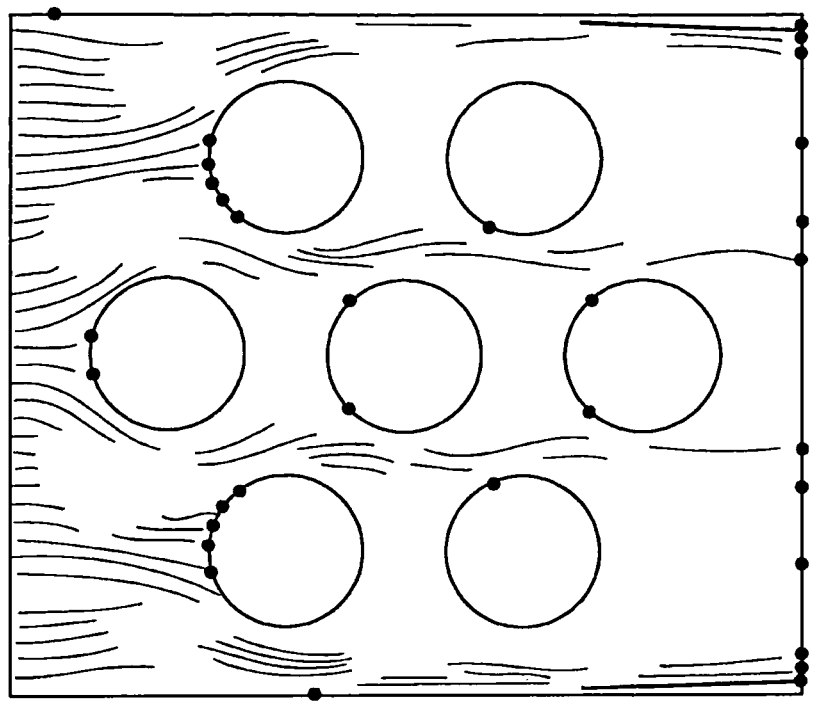
FIG. 6A is a plan view of a hexagonal arrangement of circular posts within a fluid channel.

The channel can be configured to maximize binding of the analyte complex to one or more surfaces within the channel, while permitting a desired rate of fluid flow through the channel. The posts and interior walls enclosing the channel can be coated with binding moieties selected to bind an analyte complex. In general, increasing the surface area of the posts can increase the area for analyte complex binding while increasing the resistance to sample fluid flow through the channel from the inlet to the outlet. FIG. 6A shows top view of a hexagonal arrangement of circular posts within a fluid channel. Fluid flow lines around the posts are shown and binding sites of cell complex capture are indicated by solid dots on the surface of the posts. The dimensions and positions of the posts are selected to provide a desired rate of fluid flow through the channel while maximizing the incidence of analyte capture on the surface of the channel.

Figure 6B:
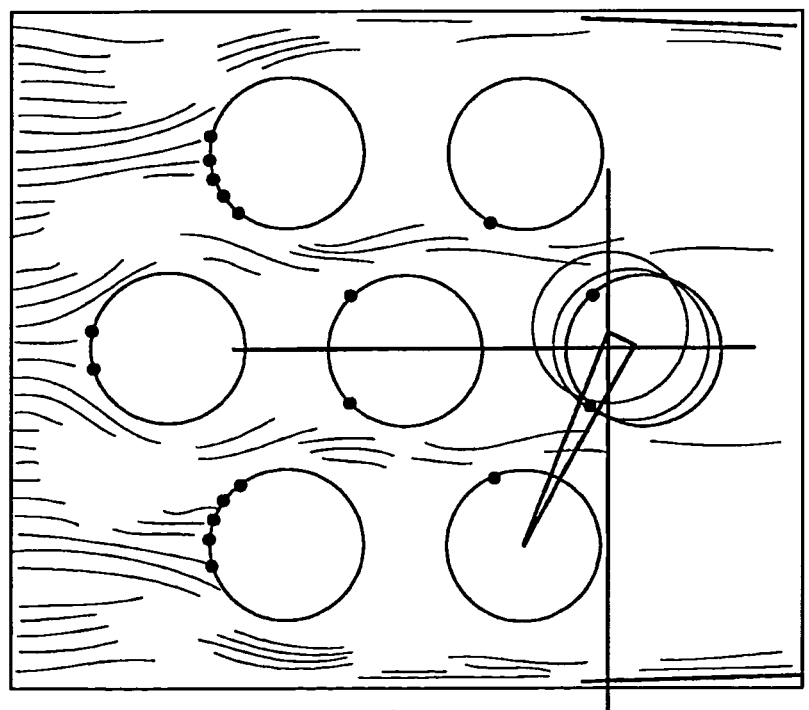
FIGS. 6B, 6C, and 6D show modifications to the hexagonal lattice of FIG. 6A to create a rotated lattice modification of the hexagonal lattice arrangement shown in FIG. 6A.
Figure 6C:
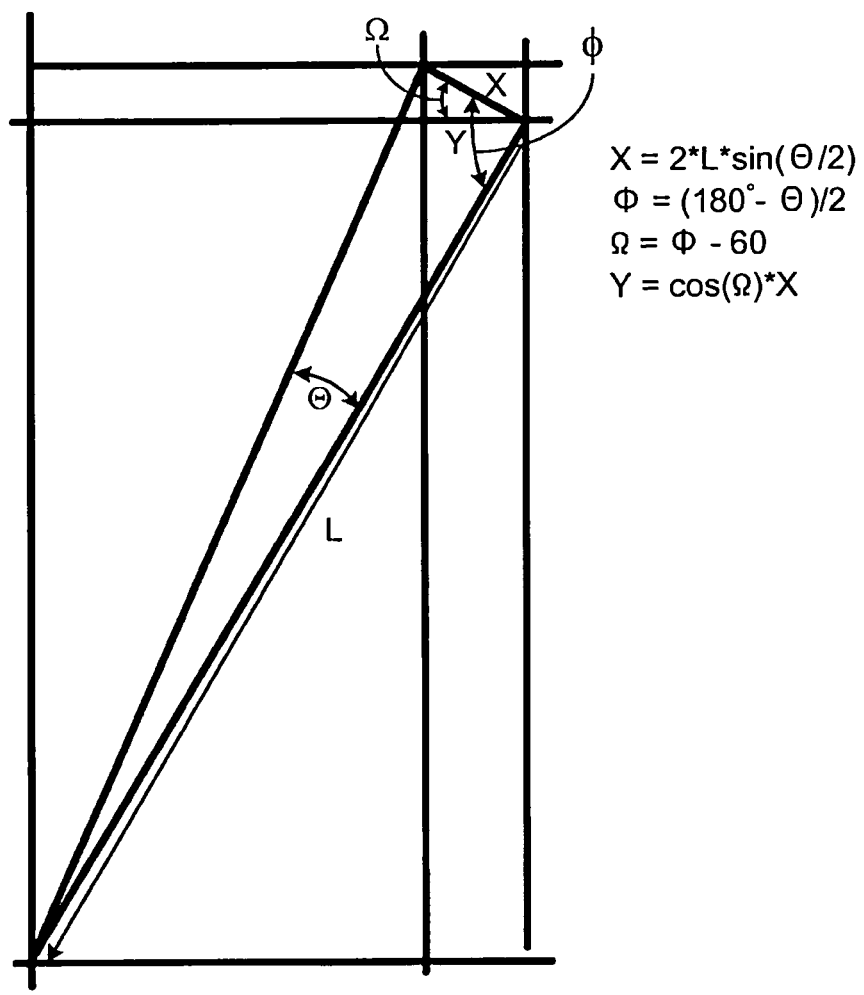
Figure 6D:
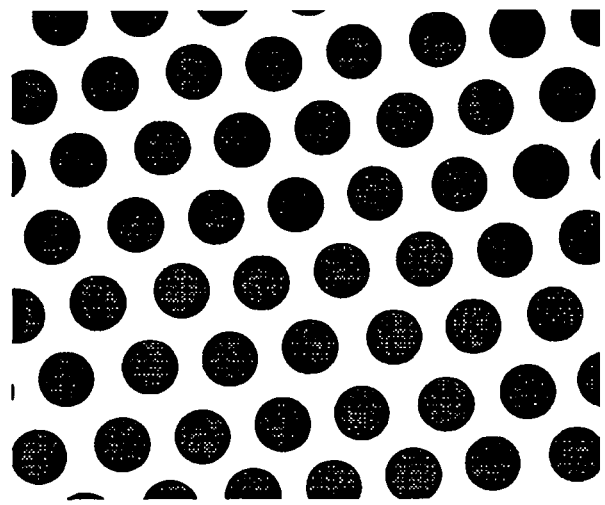

FIGS. 6B and 6C show modifications to the hexagonal lattice of FIG. 6A to create a rotated lattice modification of the hexagonal lattice arrangement shown in FIG. 6A. FIG. 6C is a schematic showing the shift of two posts relative to one another. A first line L extends from the center of a first post to the center of an adjacent post in the original lattice of FIG. 6A. A second line L extends from the center of the first post to the center of the same adjacent post in the rotated lattice. Variables X, phi, omega, and Y are geometrically defined in FIG. 6C. The fluid flow dynamics of the rotated lattice is described in more detail in Example 2. The rotated lattice results in an effective shift of each row relative to the next, increasing the interaction of cells in streamlines with the posts. Reducing the post size and spacing increases the probability that a cell will be within the capture radius of the post. In addition, reducing the post size and spacing increases the amount of capture surface achievable in the same footprint. A gap size limit where clogging becomes an issue can be avoided by providing at least a 4-20 µm gap between posts (depending on sample composition). The post size is preferably on the same order as the diameter of the analyte (e.g., the cell complex), as cell capture will be adversely affected when the post approaches the size or below of the cell. Rotating the hexagonal lattice with respect to the flow results in an effective shift of each row relative to the next and increases the effective interaction of cells with the device in the laminar flow environment. Rotating the hexagonal lattice with respect to the flow results in an effective shift of each row relative to the next and increases the effective interaction of cells with the device in the laminar flow environment. FIG. 6D shows a rotated hexagonal lattice. Two different rotated hexagonal post arrays are described in Table 1 below.

TABLE 1

| Lattice: | Hexagonal | Hexagonal |
|---|---|---|
| Rotation: | 7.5° (π/24) | 7.5° (π/24) |
| Post Height: | 100 µm | 100 µm |
| Post Diameter: | 80 µm | 50 µm |

TABLE 1-continued

| Lattice: | Hexagonal | Hexagonal |
|---|---|---|
| Post edge to edge spacing: | 40 μm | 25 μm |
| Post center to center: | 120 μm | 75 μm |

Figure 7:
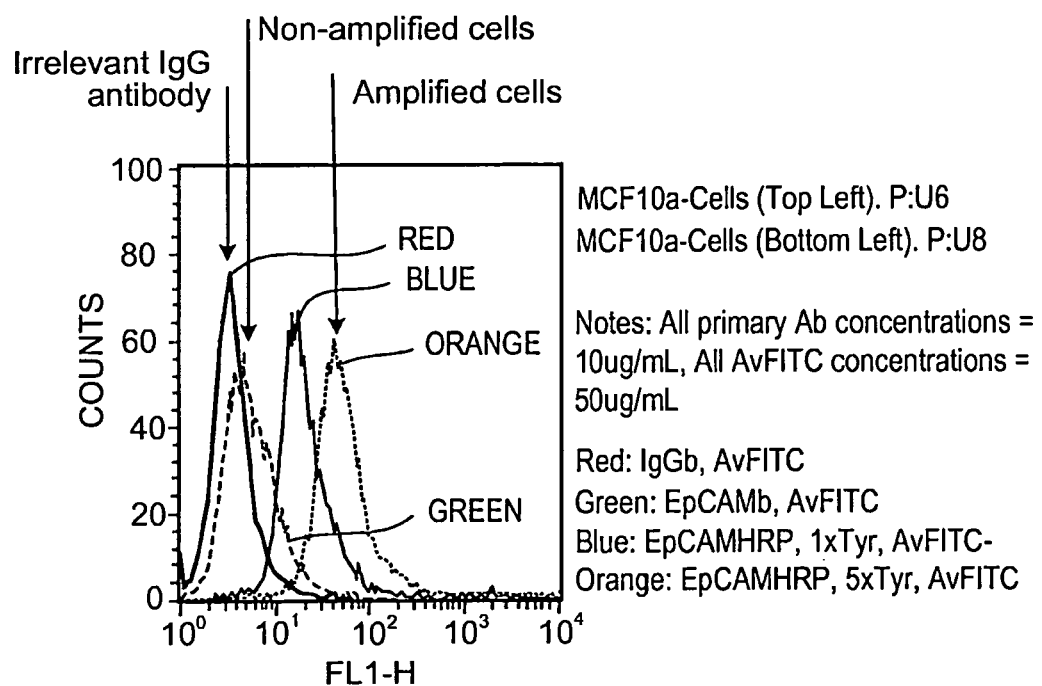
FIG. 7 is a graph that presents results of a comparative example of the amplification of a cancer cell line with ultra-low EpCAM expression.

FIG. 7 is a graph demonstrating the amplification of a cancer cell line with ultra-low EpCAM expression. Cultures of the MCF 10A cell line, a non-tumorigenic epithelial cell line, were mixed with immunoglobulin IgGb antibodies; EpCAM antibodies; and EpCAM antibody-HRP complexes. The immunoglobulin IgGb antibodies; EpCAM antibodies; and EpCAM antibody-HRP complexes were added at concentrations of 10 ug/ml. A tyramide-biotin complex was further added to the two cultures to which EpCAM antibody-HRP complexes had been added. An avidin-fluorescein isothiocyanate (FITC) complex was added to all cultures at a concentration of 50 ug/ml. The cultures to which IgGb antibodies (background) and EpCAM antibodies (non-amplified) were added were not significantly different. In contrast, amplification using a combination of the tyramide-biotin and EpCAM antibody-HRP complexes exhibited a significant increase in the cells' FITC signal. This indicates amplification in cell biotinylation, as shown using avidin-FITC.

Figure 8B:
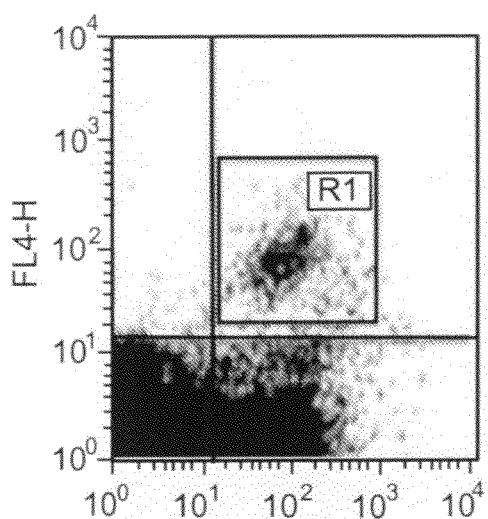
FIGS. 8B and 8C show inlet flow concentrations of direct biotinylated CTCs (FIG. 8B) and cells amplified by the methods described herein (FIG. 8C).

FIG. 8A shows the position of captured cells within a microchannel for Biotinylated Anti-human EpCAM/TROP1 Antibody (BAF960) at concentrations of 5,000 cell/mL, amplified using the tyramide-biotin and EpCAM antibody-HRP complexes approach described above at concentrations of 5,000 cells/mL, at 500 cells/mL, and at 50 cells/mL. FIGS. 8B (non-Amplified) and 8C (Amplified) show inlet biotin concentrations for the 5,000 cells/mL cases. Based on observed inlet biotin concentrations in these two graphs, the two approaches to tagging cells appeared to provide very similar results with the mean amplification value for BAF960 (5 k cells/mL)=120 and for Amp (5 k cells/mL)=111. Thus, there was no apparent benefit to using the amplification system. However, the heat maps in FIG. 8A, unexpectedly show that the "Amp" cells amplified using the new tyramide-biotin and EpCAM antibody-HRP complex methods are captured much earlier in the column than the non-amplified "BAF960" cells.

Thus, although the flow results suggested only minimal amplification, the new methods described herein provided a significant (three-fold) increase in capture efficiency. These results demonstrate that, in addition to the number of biotin molecules on a given cell, the configuration and presentation of the biotin molecules on the cell surface, e.g., in clusters, is also a critical aspect of capture efficiency in, for example, a microfluidic chip.

FIGS. 9A-9E compare positions of captured cells and timing of non-specific binding events for different flow rates and amplification parameters. The tyramide-biotin and EpCAM antibody-HRP complexes approach was used with two different levels of tyramide-biotin addition; with flow rates ranging from 1.57 mL/hr to 8.02 mL/hr; and for periods ranging from 1 to 3 minutes. As can be observed by comparing, FIG. 9A with FIGS. 9B-9E, using lower levels of tyramide-biotin complex can reduce the interference from non-specific binding events without decreasing capture efficiency. In addition, by comparing FIG. 9D with FIG. 9E, it can be observed that while increasing flow rates decreases capture efficiencies somewhat, the microfluidic chip was still able to perform adequately with a 5-fold increase in the flow rate.

Figure 10:
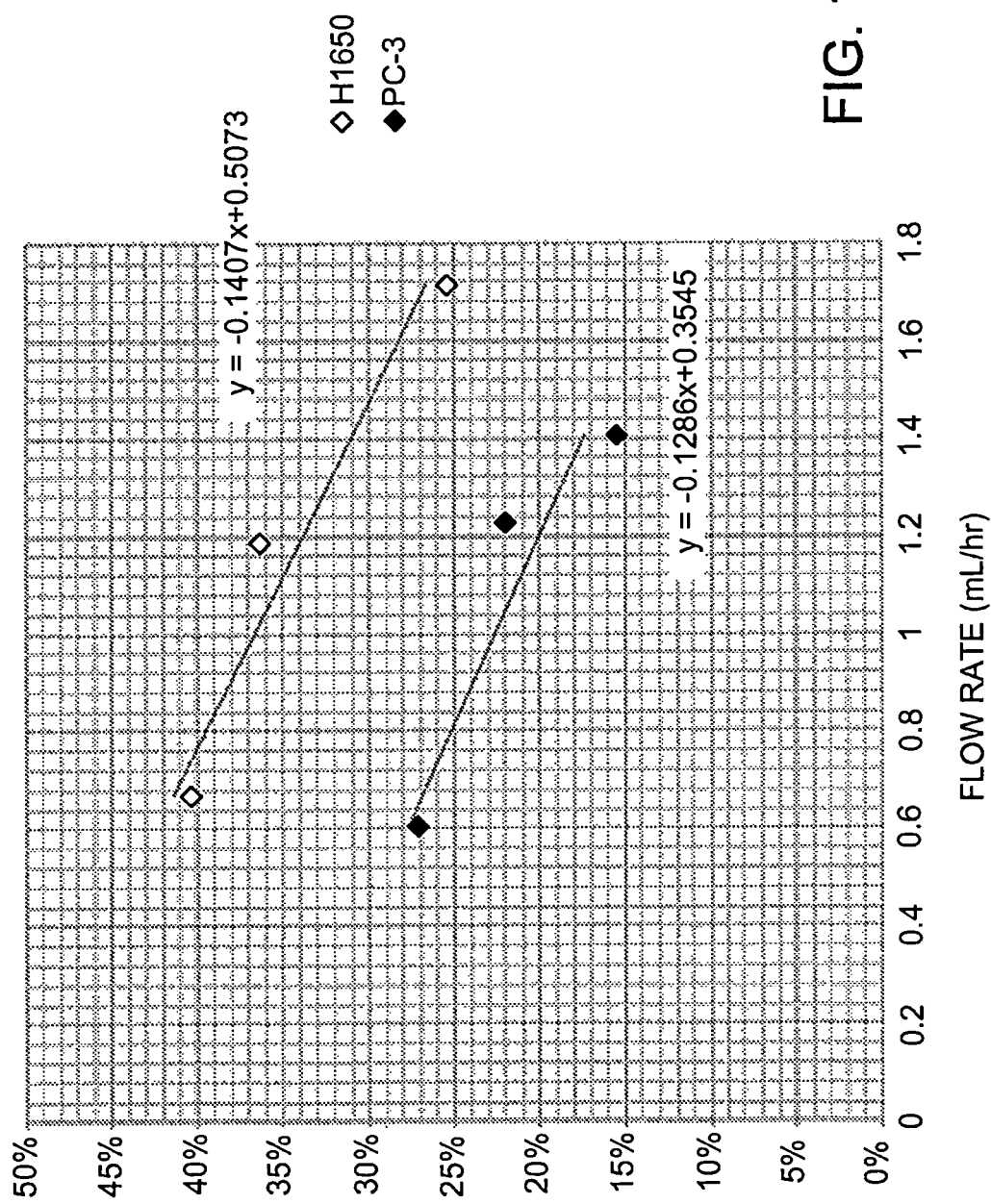
FIG. 10 is a graph showing a comparative example of antibody cell capture by a surface comprising surface-bound EpCAM antibodies in the absence of cell complex formation in the sample.

FIG. 10 is a graph showing a comparative example of antibody cell capture by a surface comprising surface-bound EpCAM antibodies in the absence of cell complex formation in the sample. Cells were biotinylated nonspecifically and captured on streptavidin. In particular, FIG. 10 shows that capture yields are adversely affected by flow rate and receptor copy number in the absence of cell complex formation. High EpCAM expressing H1650s are captured at a lower yield than lower expressing PC3-9 cells. This data was obtained by contacting the cells with a microfluidic channel coated with anti-EpCAM antibodies, as described in PCT/US2008/011785 (WO2009/051734), filed Oct. 16, 2008.

FIG. 11 shows the position of CTC cells captured within a microchannel for direct immunocapture (i.e., using a surface-bound EpCAM antibody to capture the CTC cell in the microchannel) or pre-tagged capture (i.e., using a surface-bound streptavidin to bind CTC cell complexes comprising a CTC cell, biotinylated EpCAM antibody, biotin and streptavidin). The position of the cells was identified by staining. In the case of pre-tagged capture, the capture is enhanced because antigens are specifically converted to biotins. The biotinylated cells then interact with devices modified with streptavidin and are retained at a high efficiency due to the fact that the streptavidin-biotin binding is much higher than typical antibody-antigen binding. For direct immunocapture, the capture pattern showed a shallow decay pattern in the direction of sample fluid flow. In the pre-tagged capture channel, the capture pattern showed a steeper decay pattern with a higher percentage of the CTC cell complexes captured earlier in the direction of sample fluid flow.

FIGS. 12A and 12B are another set of capture heat maps that show the position of CTCs captured in flow cells using Neutravidin modified surfaces to capture specifically (EpCAM-mediated; FIG. 12B) and nonspecifically (NHS-PEG-Biotin; FIG. 12A) biotinylated cells. FIG. 12C shows that cells can be biotinylated with varying levels of specificity using different dimensions of the targets (NHS-PEG-Biotin modifying cell surface amine groups (shown as the dot on the left in the graph), biotinylated anti-EpCAM modifying cell surfaces EpCAM, shown as the dot on the right). To obtain this data shown in FIGS. 12A and 12B, cells were pre-tagged with NHS-PEG-Biotin or biotinylated anti-EpCAM, spiked into blood and retrieved using the CTC capture chip.

Optionally, the sample can be treated prior to introduction to the channel, for example, by enriching or depleting the sample in one or more components. To reduce non-specific binding of sample components other than the analyte, the sample can be treated to remove one or more sample components that non-specifically bind to a channel surface. "Non-specific binding" refers to binding of a sample component that is not the intended analyte from the sample. For detecting CTCs in whole blood samples, the presence of white blood cells in the sample can result in an undesirably high number of white blood cells binding to the surface of a channel. Methods of improving the purity of sample components bound to a channel surface increases the number of analyte cells bound to the channel surface, improving detection of these bound analyte cells using several molecular assays such as DNA, RNA, and FISH. To improve purity, methods of CTC detection can include depletion of white blood cells from the patient samples before they are processed through the microfluidic channel for capturing the CTC analyte.

For example, a whole blood sample can be first passed through a monocyte depletion chamber, which depletes CD4+ monocytes in the blood sample (See, e.g., 61/143,316, filed Jan. 8, 2009). The monocyte-depleted blood sample passes through the microfluidic analyte capture channel, where binding analytes (e.g., biological cells) selectively bind to specific binding moieties and are retained within the channel. The blood sample can also be passed through the spiral channel, to produce a platelet enriched (leukocyte depleted) stream exiting the spiral channel through a first outlet and a leukocyte enriched (platelet depleted) stream exiting the spiral channel through the second outlet. The spiral channel can be configured to separate two or more components of a fluid sample based on relative mass, such as platelets and leukocytes. The spiral channel can be an asymmetrically curved channel described in U.S. patent application Ser. No. 12/103,885, filed Apr. 16, 2008, portions of which pertaining to the separation of particles or cells based on relative mass within an asymmetrically curved channel are incorporated herein by reference. Preferably, passing the sample through the spiral channel does not alter the activation state of the leukocyte cell population. The leukocyte enriched stream can be passed through one or more cell capture channels including binding moieties selected to bind to one or more leukocyte cells. The dimensions of each cell capture channel and the flow rate can be selected to capture and retain at least a portion of a first leukocyte cell population within a cell capture channel, thereby reducing the first leukocyte cell population in the leukocyte enriched stream. For example, the leukocyte cell population can be selected from the group consisting of: monocytes, neutrophils and lymphocytes. Separate types of leukocytes can be captured in separate cell capture chambers.

Depletion of white blood cells from a whole blood sample prior to introduction to a microfluidic channel is preferably performed one of two ways: (1) using a depletion column coated with CD45 antibody to capture white blood cells and deplete white blood cells from the sample before entering the channel (resulting in only 250-350 microliters of blood being able to be processed); (2) Depletion using techniques by Stem Cell Technologies can use 5 ml of whole blood (e.g., Easy-Sep® and RosetteSep®). Example 6 describes two methods of depleting white blood cells from a whole blood sample prior to capturing CTCs from the sample in a microfluidic channel. Using these two different depletion methods, a typical amount of 5 ml of whole blood can be used.

Manufacturing Cell Capture Chips

FIG. 13 is a schematic showing one method for forming the microfluidic channel devices disclosed herein. In this example, standard photolithography is used to create a photoresist pattern of obstacles on a silicon-on-insulator (SOI) wafer. A SOI wafer consists of a 100 µm thick Si(100) layer atop a 1 µm thick $SiO_2$ layer on a 500 µm thick Si(100) wafer. To optimize photoresist adhesion, the SOI wafers can be exposed to high-temperature vapors of hexamethyldisilazane prior to photoresist coating. UV-sensitive photoresist is spin coated on the wafer, baked for 30 minutes at 90° C., exposed to UV light for 300 seconds through a chrome contact mask, developed for 5 minutes in developer, and post-baked for 30 minutes at 90° C. The process parameters can be altered depending on the nature and thickness of the photoresist. The pattern of the contact chrome mask is transferred to the photoresist and determines the geometry of the obstacles.

Upon the formation of the photoresist pattern that is the same as that of the obstacles, the etching is initiated. $SiO_2$ may serve as a stopper to the etching process. The etching may also be controlled to stop at a given depth without the use of a stopper layer. The photoresist pattern is transferred to the 100 µm thick Si layer in a plasma etcher. Multiplexed deep etching can be utilized to achieve uniform obstacles. For example, the substrate is exposed for 15 seconds to a fluorine-rich plasma flowing $SF_6$, and then the system is switched to a fluorocarbon-rich plasma flowing only $C_4F_8$ for 10 seconds, which coats all surfaces with a protective film. In the subsequent etching cycle, the exposure to ion bombardment clears the polymer preferentially from horizontal surfaces and the cycle is repeated multiple times until, e.g., the $SiO_2$ layer is reached.

To couple a binding moiety to the surfaces of the obstacles, the substrate can be exposed to an oxygen plasma prior to surface modification to create a silicon dioxide layer, to which binding moieties can be attached. The substrate may then be rinsed twice in distilled, deionized water and allowed to air dry. Silane immobilization onto exposed glass is performed by immersing samples for 30 seconds in freshly prepared, 2% v/v solution of 3-[(2-aminoethyl)amino]propyltrimethoxysilane in water followed by further washing in distilled, deionized water. The substrate is then dried in nitrogen gas and baked. Next, the substrate is immersed in 2.5% v/v solution of glutaraldehyde in phosphate buffered saline for 1 hour at ambient temperature. The substrate is then rinsed again, and immersed in a solution of 0.5 mg/mL binding moiety, e.g., anti-CD71, anti-CD36, anti-GPA, or anti-CD45, in distilled, deionized water for 15 minutes at ambient temperature to couple the binding agent to the obstacles. The substrate is then rinsed twice in distilled, deionized water, and soaked overnight in 70% ethanol for sterilization.

There are multiple techniques other than the method described above by which binding moieties can be immobilized onto the obstacles and the surfaces of the device. Simple physio-absorption onto the surface can be the choice for simplicity and cost. Another approach may use self-assembled monolayers (e.g., thiols on gold) that are functionalized with various binding moieties. Alternatively, the binding moiety can be embedded into a hydrogel pre-polymer. The hydrogel pre-polymer can be applied and cured in-situ to form a conformal coating, providing the presentation of the binding moieties on the posts and channel surface. Additional methods can be used depending on the binding moieties being bound and the material used to fabricate the device. Surface modification methods are known in the art. In addition, certain cells may preferentially bind to the unaltered surface of a material. For example, some cells may bind preferentially to positively charged, negatively charged, or hydrophobic surfaces or to chemical groups present in certain polymers.

The next step involves the creation of a flow device by bonding a top layer to the microfabricated silicon containing the obstacles. The top substrate can be glass to provide visual observation of cells during and after capture. Thermal bonding or a UV curable epoxy can be used to create the flow chamber. The top and bottom may also be compression fit, for example, using a silicone gasket. Such a compression fit can be reversible. Other methods of bonding (e.g., wafer bonding) are known in the art. The method employed may depend on the nature of the materials used.

The channel surface can be made out of different materials. Depending on the choice of the material different fabrication techniques may also be used. The device can be made out of plastic, such as polystyrene, using a hot embossing technique. The obstacles and the necessary other structures are embossed into the plastic to create the bottom surface. A top layer may then be bonded to the bottom layer. Injection molding is another approach that can be used to create such a device. Soft lithography may also be utilized to create either a whole chamber made out of poly(dimethylsiloxane) (PDMS), or only the obstacles can be created in PDMS and then bonded to a glass substrate to create the closed chamber. Yet another approach involves the use of epoxy casting techniques to create the obstacles through the use of UV or temperature curable epoxy on a master that has the negative replica of the intended structure. Laser or other types of micromachining approaches may also be utilized to create the flow chamber. Other suitable polymers that can be used in the fabrication of the device are polycarbonate, polyethylene, and poly(methyl methacrylate). In addition, metals like steel and nickel may also be used to fabricate the device of the invention, e.g., by traditional metal machining. Three-dimensional fabrication techniques (e.g., stereolithography) can be employed to fabricate a device in one piece.

Reducing Non-Specific Binding

The non-specific binding of analytes to channel surfaces can be reduced by contacting the surface with a nonionic detergent. This can be done before and/or after contacting a sample with a channel surface.

In one example, non-specific binding of analytes to channel surfaces is reduced by contacting the surface comprising the analyte-binding moiety with a nonionic detergent prior to sample contact with the surface. The nonionic detergent can be a polysorbate surfactant such as a polyoxyethylene derivative of sorbitan monolaurate (e.g., polysorbate 20, sold under the tradename TWEEN 20®). Other polysorbates include the following which are available commercially: Polysorbate 40 (TWEEN 40®), Polysorbate 60 (TWEEN 60®), and Polysorbate 80 (TWEEN 80®). The nonionic detergent can be contacted with the surface at a concentration lower than the concentration required to lyse mammalian cells. For example, an aqueous solution comprising polysorbate 20 at a concentration of up to about 0.05% can be used to pre-treat a surface before contact with a biological sample. The aqueous solution can further comprise components to reduce non-specific surface binding from blood components.

For example, the surface can be contacted with a mixture of 0.05% polysorbate 20, 1% BSA and 1× phosphate buffered saline (PBS) (calcium ion and magnesium ion—free). The volume of the pre-treatment solution can be selected based on the dimensions of the channel. For example, about 3 mL of the 0.05% polysorbate 20 solution described above can be passed through a microfluidic channel at a rate of about 30 ml/hr. The microchannel can be incubated in the polysorbate 20 solution for about 1 hour before introducing the biological sample to the channel. Example 3 compares the cell-binding results in a microfluidic channel with and without using the polysorbate 20 solution before introducing a blood sample into the channel. The microchannel can be incubated in the polysorbate 20 solution for about 1 hour before introducing the biological sample to the channel. Example 3 compares the cell-binding results in a microfluidic channel with and without using the polysorbate 20 solution before introducing a blood sample into the channel. For example, a microfluidic channel having a surface containing a biotin-binding conjugate can be contacted with a solution comprising 0.05% Tween20 in 1% BSA in 1×PBS ($Ca^{2+}/Mg^{2+}$—free) (e.g., 3 mL of the surfactant solution at a flow rate of about 30 mL/hr) prior to contact with the biological sample containing CTCs, a biotinylated EpCAM antibody, biotin and streptavidin. Pluronics, poloxymer, PEG, and other similar surfactants can be similarly used instead of or in combination with polysorbate 20.

In another example, the non-specific binding of analytes to channel surfaces can be reduced by contacting the surface and/or analyte components bound to the surface with a nonionic detergent after contacting the surface with the biological sample (a "post-treatment solution"). The nonionic detergent can be a polysorbate surfactant such as a polyoxyethylene derivative of sorbitan monolaurate (e.g., polysorbate 20, sold under the tradename TWEEN20), preferably at a concentration lower than the concentration required to lyse mammalian cells. The nonionic post-treatment solution is passed through the channel at a rate sufficient to reduce nonspecific binding, while minimizing the removal of specifically bound analyte components. The fluid flow rate is typically slower than the rate of fluid flow rate for the pre-treatment solution, used before contacting the channel with the sample. For example, an aqueous solution comprising polysorbate 20 at a concentration of up to about 0.05% can be used contacted with a surface after contact with a biological sample. For example, the surface can be contacted with a mixture of 0.05% polysorbate 20 and 1× phosphate buffered saline (PBS) (calcium ion and magnesium ion—free) (e.g., add 2.5 uL of tween 20 to 5 mL of 1×PBS without Ca2+/Mg2+ ions). The volume of the post-treatment solution can be selected based on the dimensions of the channel. For example, about 0.7 mL of the polysorbate 20 solution described above can be passed through the channel (after the sample) at 3 mL/hr, followed by a final 0.2 mL volume of the solution at 10 mL/hr. Examples 4A-5B compare the cell-binding results in a microfluidic channel with and without using the polysorbate 20 solution after introducing a blood sample into the channel. Once non-specific binding components are removed from the channel, the remaining bound analytes remain captured on the surface of a channel, and these analytes can be subsequently detected or analyzed.

Captured Cell Analysis

Captured cells can be counted by any method known in the art, including optical, e.g., visual inspection, automated counting, microscopy based detection, and FACS, and electrical detection, e.g., Coulter counters. Counting of the cells, or other analytes, isolated using the methods and devices described herein can be useful for diagnosing diseases, monitoring the progress of disease, and monitoring or determining the efficacy of a treatment. Cell, or other analyte, counting can also be of use in non-medical applications, e.g., for determination of the amount, presence, or type of contaminants in environmental samples (e.g., water, air, and soil), pharmaceuticals, food, or cosmetics.

In another embodiment, cells isolated using the methods and devices of the invention can be lysed, and one or more properties of the cells, or portions thereof, can be measured. Examples of biological properties that can be measured in isolated cells include mRNA expression, protein expression, and DNA quantification. Additionally, the DNA of cells isolated by the methods of the invention can be sequenced, or certain sequence characteristics (e.g., polymorphisms and chromosomal abnormalities) can be identified using standard techniques, e.g., FISH or PCR. The chemical components of cells, and other analytes, may also be assayed after isolation. Cells may also be assayed without lysis, e.g., using extracellular or intracellular stains or by other observation, e.g., morphology or growth characteristics in various media. When lysis is employed, CTCs can be lysed while still bound to the chip, e.g., with any other cells nonspecifically retained. The ability to lyse CTCs on chip and obtain useful genetic information is made possible by the high purity of samples (typically greater than 50%) using the devices and methods of the invention.

Particular genetic information that can be obtained from a tumor cell captured by a CTC-chip includes identification or enumeration of particular genomic DNA, cDNA, or mRNA sequences; identification or enumeration of cell surface markers; and identification or enumeration of proteins or other intracellular contents that is indicative of the type or presence of a particular tumor. For example, CTCs can be analyzed to determine the tissue of origin, the stage or severity of disease, or the susceptibility to a particular treatment. For example, a diagnostic indicator for lung cancer and other cancers is the presence or absence of certain mutations in EGFR (see, e.g., International Publication WO 2005/

094357). Another example is assaying for HER2 to determine prognosis or treatment regimen in breast cancer. (Gynecol Obstet Fertil. 2006 July-August; 34(7-8):638-46. Epub 2006 Jul. 28) also Breast Cancer Res. 2007 Oct. 26; 9(5):R74.

We have also described herein that prostate specific antigen (PSA), a known marker for prostate cancer, can be detected in CTCs. It is detectable by protein expression staining using antibodies that measure PSA expression within cells captured on the chip (immunofluorescence and immunohistochemistry), and it is also detectable by reverse transcription polymerase chain reaction (RT-PCR) in RNA extracted from the CTCs. While measurement of PSA protein levels in blood is a standard marker for advanced prostate cancer, the ability to measure PSA levels within CTCs brings a significant measure of increased sensitivity. This increased sensitivity can be particularly important in the detection of invasive disease, since borderline PSA protein levels in the blood often lead to confusion, whereas presence of PSA-expressing CTCs in the blood can be an indicator of invasive disease.

CTCs captured by the devices and methods described herein may also be assayed for the presence of markers indicative of cancer stem cells. Examples of such markers include CD133, CD44, CD24, epithelial-specific antigen (ESA), Nanog, and BMI1.

Methods for isolating and detecting living cells in a sample can include releasing a viable bound cell from a channel surface. The binding conjugate can be attached to the surface of a channel in a manner that permits release of the conjugate capture agent from the surface after capture of the analyte. For example, the binding conjugate can be releasably adhered to the surface with one or more chemical bonds that can be broken in response to changes in, e.g., temperature, pH, ionic strength, or introduction of an additional chemical compound to the channel. The method of removing the binding conjugate from the surface can be performed in a manner that does not kill the captured living cells. Accordingly, the surface of a channel can be coated with a removable material comprising the conjugate capture agent prior to contacting the conjugate capture agent with a multivalent analyte binding agent in a biological sample. The conjugate capture agent is contacted with the multivalent analyte binding agent in the biological sample within the channel to capture an analyte in the biological sample by binding the multivalent analyte binding agent to the surface-bound conjugate capture agent. The sample can be subsequently removed from the channel, leaving the analyte bound to the surface via the bond between the multivalent analyte binding agent and the surface-bound conjugate capture agent. Subsequently, the conjugate capture agent can be released from the surface, for example by heating the surface to a temperature effective to melt the removable material containing the conjugate capture agent adhered to the surface, the temperature being low enough to preserve the viability of the captured analyte after release from the surface. The analyte can be resuspended in a solution and removed from the channel. The analyte is preferably a viable cell, such as a circulating tumor cell.

A further method for capturing circulating, non-hematopoietic tumor cells includes passing a blood sample of less than 4 mL through a microfluidic channel to which is bound a tumor specific binding agent so that circulating tumor cells in said blood sample bind to said binding agent. The invention also features a method of obtaining genetic information from a subject with a tumor by obtaining 1 to 1500 circulating tumor cells from a blood sample of 1 mL or less from the subject and assaying the cells for genetic information. For example, at 5, 10, 25, 50, 100, 200, 500, or 1000 CTCs can be obtained per mL.

Cancers that can be detected using the devices of the described herein include prostate, lung, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

Further features and aspects of the present invention are described in the following exemplary and non-limiting examples.

EXAMPLES

Example 1

Specific Binding of Cells in Microfluidic Channel

The following protocol was used to enhance specific binding of cells within a channel by increasing the number and strength of interactions solution prior to contacting the channel with a cell sample. The channel was initially coated with a cell-binding material (e.g., anti-EpCAM antibody or neutravidin bound to the surface of the channel and/or posts within the channel) prior to initiating the protocol below:

EpCAM positive H1650 cells (ATCC# CRL-5883) were maintained and prepared for pre-tagging experiments according to manufacturer's recommendations (American Type Culture Collection).

Cells were used either:
  Untagged
  Pre-tagged via cell surface amines with NHS-PEG$_4$-Biotin (Thermofisher) according to manufacturer's instructions (Thermofisher document 1299.4)
  Pre-tagged via cell surface EpCAM with 3 μg/mL biotinylated anti-EpCAM (R&D Systems) for 30 minutes, followed by a spindown and wash to remove excess antibody.

Cells were spiked into whole blood or buffer at a frequency of $10^4$ mL$^{-1}$.

The channel was first primed by passing a solution of 1% BSA in PBS (standard conditions, 3 ml at 30 ml/hr) through the channel.

A spiked blood or buffer sample (e.g., ~2-3 mL of healthy donor blood) was passed through the channel at a flow rate (e.g., ~1-2 ml/hr) appropriate to capture bind the cells to the cell-binding material on the surface of the channel.

After cell capture within the channel, the channel was rinsed with 10 mL 1×PBS without Ca2+/Mg2+ at a flow rate of about 10 mL/hr.

After rinsing cells were fixed to the channel (4% paraformaldehyde), permeabilized (0.2% Triton-X 100), and stained with a phycoerythrin labeled antibody against the epithelial cell marker cytokeratin (BD Biosciences) and nuclear counterstain DAPI (Invitrogen).

Samples were scanned using an automated microscope (Bioview) to identify the captured target cells based on positive scoring for both cytokeratin and DAPI. Typical heat maps for particular combinations of matrix, target cell, and cell capture agent are contained in Figure X. Nominal yields typically fall in a range from 30-60% depending on exact conditions (flow rate, hematocrit, etc.), but these values were determined to be inaccurate in some cases due to the significant undercounting that can occur at high capture efficiencies (i.e. capture of pre-tagged cells) when significant overlap of captured cells is observed. Qualitatively, the results clearly demonstrate that pre-tagging has a significant positive impact as judged by the fact that the cells are captured much earlier in the device. Both specifically (anti-EpCAM-biotin) and non-specifically (NHS-PEG$_4$-Biotin) pre-tagged cells exhibit steeper capture profiles than those observed on direct immunocapture of untagged cells. Surprisingly, a comparison of the NHS-PEG$_4$-Biotin pre-tagged cells indicates that a similar effect is observed in both simple (buffer) and complex (whole blood) matrices.

Example 2

Analyte Capture Using a Rotated Lattice Microchannel Post Array

A series of cell capture simulations were performed on the rotated lattice formation shown in FIGS. 6B-6D. The data is provided in Table 2 below. The rotated lattice modeling includes a register shift every row of posts to provide better efficiency of analyte-post interaction by resetting streamlines with higher frequency, and providing a higher array density to maximize analyte-post interactions without compromising the volumetric flow rate.

Two protocols were compared: a "Tween pre-wash" protocol and a "Standard" protocol. The steps in the "Tween" protocol were: (1) Purge chip with 0.05% Tween20 in 1% BSA in 1×PBS (Ca$^{2+}$/Mg$^{2+}$—free) with a total volume of 3 mL at a flow rate of 30 mL/hr; (2) incubate at room temperature for 1 hour; and (3) initiate whole blood flow through chip. The "Standard" protocol steps were: (1) Purge chip with 1% BSA in 1×PBS (Ca$^{2+}$/Mg$^{2+}$—free) with a total volume of 3 mL at a flow rate of 30 mL/hr; and (2) initiate whole blood flow through the channel.

FIG. 14 shows a reduction of 87±1% in NSB from control condition. To obtain the data shown in FIG. 14, we processed healthy donor samples using the "Tween" and "Standard" protocols described in the "Tween pre-wash" and "Standard" protocols above. For each condition, 5 mL of donor blood was processed post-wash step and subsequently stained against cytokeratins 7/8, CD45, and DNA (DAPI) using the protocol outlined in Nagrath et al. (supra) and incorporated herein by reference. To enumerate the amount of non-specific binding, chips were scanned and analyzed as described in Examples 7A and 7B. For healthy donors, cells captured on the CTC-chip were defined as 'non-specifically bound' if they were positive for DNA (DAPI) and negative for cytokeratin. Donor samples were obtained from an adult male (HD1) and female (HD2).

FIG. 15 shows the impact of the Tween pre-wash protocol (discussed above) on the number of "false positives" in healthy donor samples "HD1" and "HD2." To obtain the data shown in FIG. 15, any cell captured on the CTC-chip was defined as a 'false positive' event if the cell was positive for DNA (DAPI), and cytokeratin and negative for CD45. For both samples, the total number of false positives was below the 'significance' threshold of 15 CTCs/mL. This significance threshold was obtained from averaging the counts of 10 healthy donors stained for cytokeratin and CD45 and enumer-

TABLE 2

| User Defined Lattice Rotation (degrees) 7.5 | | | | | | | | | |
|---|---|---|---|---|---|---|---|---|---|
| Converted Lattice Rotaion (radians) 0.13 | | | | | | | | | |
| D (post diameter, µm) | L (center to center, µm) | X (gap, µm) | Row Spacing (µm) | Relative Row Packing | Shift (µm) | Post Area/unit cell (µm2) | Total Area/unit cell (µm2) | Open Area unit cell (µm2) | % Open Area |
| 100 | 150 | 50 | 130 | 1.00 | 17.6 | 3927 | 9743 | 5816 | 0.60 |
| 90 | 135 | 45 | 117 | 1.11 | 15.8 | 3181 | 7892 | 4711 | 0.60 |
| 80 | 120 | 40 | 104 | 1.25 | 14.1 | 2513 | 6235 | 3722 | 0.60 |
| 70 | 105 | 35 | 91 | 1.43 | 12.3 | 1924 | 4774 | 2850 | 0.60 |
| 60 | 90 | 30 | 78 | 1.67 | 10.6 | 1414 | 3507 | 3507 | 0.60 |
| 50 | 75 | 25 | 65 | 2.00 | 8.8 | 982 | 2436 | 1454 | 0.60 |

This exemplary cell post design keeps open area fixed (determined by the unit cell geometry). Designs with the same open area had similar flow resistance, and designs with the same open area can require similar DRIE processes.

Example 3

Polysorbate20 Pre-Wash to Reduce Non-Specific Binding (NSB)

Figure 8C:
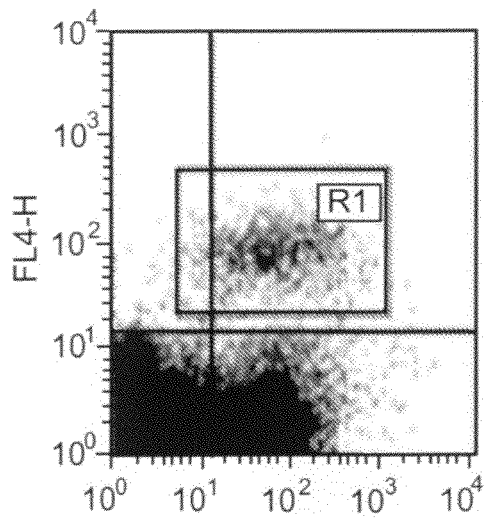
Figure 9A:
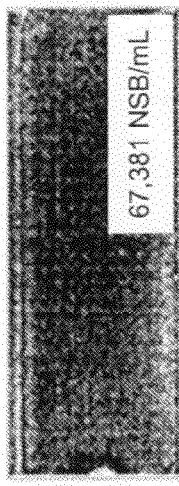
FIGS. 9A-9E are capture heat maps that compare positions of captured cells and non-specific binding events for different flow rates and amplification parameters.
Figure 9B:
Figure 9C:
Figure 9D:
Figure 9E:

The microfluidic device described in Nagrath et al., Nature, 450:1235-1239 (2007) (incorporated herein by reference in its entirety) was used to evaluate the binding of cellular sample components to a surface coated with an antibody to EpCAM.

ated on our automated imaging platform From the data shown in FIGS. 8 and 9, we conclude that the Tween pre-wash dramatically decreases non-specific binding (FIG. 14), and does not have a significant impact on the number of false positives in healthy donor samples (FIG. 15).

FIG. 16 shows a reduction of 78±3% in NSB from control condition. To obtain the data shown in FIG. 16, we processed blood from cancer patients with various disease states, splitting the sample between two CTC-chips, using either the Tween pre-wash or standard protocol (see described in the "Tween pre-wash" and "Standard" protocols above). For each chip, a minimum of 4 mL of blood was processed and subsequently stained against cytokeratins 7/8, CD45, and DNA (DAPI) using the protocol outlined in Nagrath et al., Nature 450 (2007). Similar to the "Tween pre-wash" and "Standard" protocols above, 'non-specifically bound' cells were defined as captured cells that were staining positive for DNA (DAPI) and negative for cytokeratin. The impact of 0.05% tween priming protocol on non-specific binding was assessed in patient samples obtained ELU=Early Lung, GU=Prostate, MGH=Lung, TH=Lung, DCFI=Lung cancer cells. From the data shown in FIG. 16, we conclude that the Tween pre-wash step significantly reduces NSB in patient samples.

FIG. 17 shows the impact of the Tween protocol on cell capture (CTCs) from patient samples. To obtain the data shown in FIG. 17, we enumerated all captured cells that were positive for cytokeratin, and negative for CD45. The data shown in FIG. 17 shows the majority of tween-primed samples had equivalent or better performance in target cell capture in comparison to standard blocking conditions. In particular, the data showed (Note: all patients studied were at various stages of treatment):

5:8 (62.5%) had an increase in CTC capture with the tween priming protocol

2:8 (25%) had zero capture for both the control and tween conditions

1:8 (12.5%) had a decrease in CTC capture with the tween priming protocol

From the data shown in FIG. 17, we conclude that priming the chip with surfactant reduces binding of unwanted analytes.

Example 4A

Polysorbate20 Wash of Captured Cells to Reduce Non-Specific Binding (NSB)

This example demonstrates the reduction in non-specific binding as a result of contacting cells captured on a surface with a nonionic detergent. In particular, we contacted cells bound by anti-EpCAM antibodies with a polysorbate20 non-ionic detergent to reduce non-specific binding to the surface by about 99.8%. This example describes a "Tween post-wash" protocol performed to reduce non-specific binding after contacting a microfluidic channel with a sample.

A non-ionic detergent solution ("1×PBS with tweed") for washing captured cells was prepared as follows: add 2.5 uL of Polysorbate 20 to 5 mL of 1×PBS (without Ca2+/Mg2+); vortex and store in water bath until ready for use. This solution can be sonicated prior to heating, but should not be filtered prior to contact with bound cells. The polysorbate 20 detergent solution can be stored in 37° C. water bath until immediately ready to load into a channel.

The following protocol ("Tween post-wash protocol") was used to reduce non-specific binding of cells within a channel using the non-ionic polysorbate 20 detergent solution after contacting the channel with a cell sample. The channel was initially coated with a cell-binding material (e.g., anti-Ep-CAM antibody bound to the surface of the channel and/or posts within the channel) prior to initiating the Tween post-wash protocol below:

The channel was first primed by passing a solution of 1% BSA in PBS (standard conditions, 3 ml at 30 ml/hr) through the channel.

A blood sample (e.g., ~2-3 mL of healthy donor blood) was passed through the channel at a flow rate (e.g., about 1 ml/hr) appropriate to capture bind the cells to the cell-binding material on the surface of the channel.

After cell capture within the channel, the channel was rinsed with 10 mL 1×PBS without Ca2+/Mg2+ at a flow rate of about 10 mL/hr. During this step, the Polysorbate20 detergent solution described above can be prepared for immediate introduction to the channel after completion of the wash step. This is important to prevent NSB cells from forming stronger bonds to the channel surface.

About 0.7 mL of the polysorbate 20 detergent solution described above (1×PBS with Tween polysorbate 20 at 0.05%) is immediately passed through the channel at 3 mL/hr, followed by final volume of 0.2 mL of the same solution at 10 mL/hr. Immediately thereafter, the microfluidic device containing the channel is moved to incubator for 40 minutes. The temperature of the fluid in the channel is maintained at or near 37 deg. C.

After incubation is complete, the microfluidic device channel is immediately rinsed with 6 mL 1×PBS without Ca/Mg, at a rate of 10 mL/hr.

Fix the remaining cells bound to the surface microfluidic device channels (if staining) and complete remainder of standard chip processing protocol.

The protocol above was performed using a microfluidic channel using a whole blood sample from healthy donors. The amount of non-specific binding was enumerated in the same manner as presented in Example 3. The data shown in FIG. 18 shows a 99.8% reduction of non-specific binding in a healthy donor control chip using the polysorbate20 post cell-binding wash protocol described above.

Example 4B

Polysorbate20 Wash of Captured Cells to Reduce Non-Specific Binding (NSB)

This example demonstrates the reduction in non-specific binding using the Tween post-wash protocol from Example 4A (i.e., polysorbate20 non-ionic detergent applied after cell binding in a microchannel, as described in Example 4A), using a sample obtained from (healthy) whole blood with Spiked Cells (H1650's).

One donor sample split between four chips: one control chip (standard processing protocol), and three 'tween post-wash chips' with variations in incubation time (20 min at 37 C or 40 min at 37 C). For all samples, the healthy donor blood was pooled into one volume with pre-labeled (CMRA at 0.5 µM) H1650 cells at a spiking density of 5,000 cell/mL of whole blood. After spiking, the blood was split between the four chips. To evaluate the percentage of cells that were removed due to the change in protocol, all effluent was collected from each chip and fixed in 4% paraformaldehyde. For each condition, the number of cells remaining on the chip and the number of cells in the effluent was determined. From these two values, the percentage of cell loss due to the subsequent processing was determined:

Control condition: 3% cell loss (presumably due to buffer flow).

Trypsin post-wash, 20 min incubation: 4% cell loss

Trypsin post-wash, 40 min incubation "A": 6% cell loss

Trypsin post-wash, 40 min incubation "B": 7% cell loss

The results of the experiment are presented in FIG. 19, demonstrating the impact of Tween post-wash on NSB and spiked cell capture. One patient donor sample was used, split between four conditions: control, Tween post-wash with 20 minute incubation and Tween post-wash with 40 minute incubation (×2). A dramatic reduction in NSB was measured in all Tween post-wash chips, with a slight reduction in spiked cell capture (percent reduction is noted in text above each condition). For the control condition, a sham buffer (1×PBS) was used in place of the Tween wash buffer.

FIGS. 20A and 20B are representative micrographs illustrating the condition of spiked cells in the Tween post-wash chip (20A) and control chip (20B). No adverse effect of the Tween post-wash was evident.

Example 5A

Polysorbate20 Wash of Captured Cells to Reduce Non-Specific Binding (NSB) Using Samples from Subjects Diagnosed with Cancer Disease State This example demonstrates the reduction in non-specific binding using the polysorbate 20 non-ionic detergent protocol after cell binding in a microchannel, as described in Example 4A, using a sample obtained from whole blood from early stage breast cancer patient. Circulating tumor cells were captured from the whole blood in the microfluidic channel using surface-bound Human Anti-EpCAM.

Results from measurements of non-specific binding in the microfluidic channel with and without performing the polysorbate20 non-ionic detergent wash after cell binding are shown in FIGS. 21A-21B (i.e., "post wash chip" refers to the microchannel washed after cell binding using the Example 4A protocol). FIG. 21A shows the reduction in non-specific binding in an early stage lung cancer patient and FIG. 21B shows the increase in target cell capture in the Tween post-wash chip in comparison to the control chip.

Washing bound CTC cells in the microchannel with polysorbate 20 non-ionic detergent according to the protocol of Example 4A reduced non-specific binding to the surface-bound anti-EpCAM antibody by 98.8%. Target cell capture increased slightly when using the polysorbate 20 non-ionic detergent post-wash protocol of Example 4A. Bound CTC cells were detected in the microchannel with Keratin/CD45 stain.

Example 5B

Polysorbate20 Wash of Captured Cells to Reduce Non-Specific Binding (NSB) Using Samples from Subjects Diagnosed with Cancer Disease State This example demonstrates the reduction in non-specific binding using the polysorbate20 non-ionic detergent protocol after cell binding in a microchannel, as described in Example 4A (except that a 30 minute incubation time was used instead of the standard 40 minute time), using a sample obtained from whole blood from a mouse with pancreatic cancer. Circulating tumor cells were captured from the whole blood in the microfluidic channel using surface-bound Anti-mouse EpCAM.

Results from measurements of non-specific binding in the microfluidic channel with and without performing the polysorbate 20 non-ionic detergent wash after cell binding are shown in FIGS. 22A-22B (i.e., "post wash chip" refers to the microchannel washed after cell binding using the modified Example 4A protocol described above). FIG. 22A shows the reduction in non-specific binding in blood from a mouse with pancreatic cancer. FIG. 22B shows an increase in target cell capture in the post-wash chip all in comparison to the control chip.

Washing bound CTC cells in the microchannel with polysorbate 20 non-ionic detergent according to the protocol of Example 4A reduced non-specific binding to the surface-bound anti-mouse EpCAM antibody by 75%. Target cell capture increased slightly when using the polysorbate 20 non-ionic detergent post-wash protocol of Example 4A. Bound CTC cells were detected in the microchannel with EGFR/CD45 stain.

Example 6

Pre-Depletion of White Blood Cells from Whole Blood with H1650 Cells

A spiked cell experiment was run comparing two methods for depletion of white blood cells prior to introduction to a channel for CTC capture, along with a control. The sample included H1650 cells spiked into healthy blood at a concentration of 5,000/ml. All three conditions used synthetic chips and were stained with Cam 5.2 and BD CD45. All chips were then scanned on the bioview fluorescent microscope A first depletion method involved first lysing 5 ml of whole blood and then spun in a centrifuge for 5 minutes at 350 g followed by a wash step and then finally re-suspending it in a depletion buffer of PBS 2% FBS and 1 mM EDTA. Then a CD45 antibody complex which binds to the white blood cells is added to the solution and incubated for 15 min, then followed by adding magnetic nanoparticles which bind to the CD45 antibody complex and left to incubate for 10 min before placing in a magnet. The intensity of the magnet is 1 tesla. The solution is then poured out while the tube remains in the magnet so that the white blood cells remain stuck to the side of the tube. One commercially available example of the first depletion method is sold under the tradename EasySep®.

A second depletion method was carried out by adding the antibody cocktail to 4.5 ml of whole blood and incubating for 20 minutes. The antibody cocktail crosslinks the white blood cells to the red blood cells to create "immunorosettes" the sample is then diluted with the same depletion buffer used for the EasySep depletion, suspended over a dense medium, and then spun in a centrifuge for 20 minutes at 1200 g, the immunorosettes then sink to the bottom and the target cells can be collected at the interface between the plasma and the dense medium. One commercially available example of the first depletion method is sold under the tradename RosetteSep®.

Table 3 below shows the results comparing WBC depletion by the first and the second methods described above. While both depletion methods had a higher purity than the control chip, the second method had a much higher purity of 82% of all DAPI (4',6-diamidino-2-phenylindole) positive cells were target cells, there was a reduction in NSB of 97-99% compared to the control. Also of note was the yield for the second method was actually higher than the control while it was cut in half for the first method.

TABLE 3

| Chip | Volume (mL) | Flow Rate (mL/hr) | Total H1650s run | CK +/mL | CD45 +/mL | DAPI +/mL | Yield | Purity (ALL DAPI) | Purity (Stained cells) |
|---|---|---|---|---|---|---|---|---|---|
| Chip 1 | 4.31 | 2.155 | 21,550 | 322 | 3944 | 6064 | 6.4% | 5.3% | 7.3% |
| Chip 2 - First Method | 3.24 | 1.62 | 16,200 | 148 | 442 | 672 | 3.0% | 22.1% | 23.8% |

TABLE 3-continued

| Chip | Volume (mL) | Flow Rate (mL/hr) | Total H1650s run | CK +/mL | CD45 +/mL | DAPI +/mL | Yield | Purity (ALL DAPI) | Purity (Stained cells) |
|---|---|---|---|---|---|---|---|---|---|
| Chip 3 - Second Method | 2.23 | 1.115 | 11,150 | 694 | 39 | 846 | 13.9% | 82.0% | 92.5% |

FIGS. 23A-23C are three heat maps showing binding of DAPI positive cells in a microfluidic channel (i.e., each dot represents a DAPI positive bound cell); the top each heat map is the channel inlet. Significantly fewer DAPI positive cells bound to both the first method (EasySep) and the second method (RosetteSep). FIGS. 24A-24C are three heat maps for all the target cells found on the microchannels. Each dot in FIGS. 24A-24C represents a CAM5.2 (target CTC) Positive cells. The EasySep and RosetteSep chips follow the expected decay pattern of capture while the control chip has target cells found throughout the chip.

As summarized in Table 4 below, a total of 5 experiments were performed, all with the same conditions of H1650 cells spiked into blood at 5,000/ml and the same stain. We found that there is a 72% average drop in yield for the first (EasySep) method with only a 2 fold increase in purity. The second (RosetteSep) method had a 51% decrease in yield but a 6 fold increase purity.

TABLE 4

| Condition | CK +/mL | CD45 +/mL | DAPI +/mL | Yield | Purity (ALL DAPI) | Purity (Stained Cells) |
|---|---|---|---|---|---|---|
| Control | 825.1 | 7978.5 | 9997.7 | 17% | 11% | 16% |
| EasySep | 280.9 | 585.2 | 1056.9 | 6% | 28% | 31% |
| RosetteSep | 634.7 | 357.9 | 1268.9 | 13% | 61% | 69% |

Both depletion strategies work to significantly decrease NSB in the channel. The second method described above is preferred over the first method for pre-depletion of whole blood samples prior to detection of CTCs in a microchannel having a capture surface comprising anti-EpCAM antibodies bound to the surface for CTC capture.

Example 7A

CTC Analysis and Staining

This example describes the detection of circulating tumor cells bound to a microchannel surface. Whole blood was processed through the CTC-chip at flow rates of 1-2 mL/hr. Following a wash with saline (10 mL/hr) to remove non-specifically bound leukocytes, captured CTCs were fixed with 4% paraformaldehyde, and subsequently permeabilized with 0.2% Triton X-100 in 1% bovine serum albumin (BSA), all in phosphate buffered saline (PBS). Cells were immunostained with a monoclonal antibody against cytokeratin7/8 (BD Biosciences) followed by a secondary Alexa Fluor 488 conjugated goat anti-rabbit antibody (Invitrogen) to identify epithelial cells. CD45 expression was detected using a mouse anti-CD45 antibody (BD Biosciences) followed by Alexa Fluor 594 conjugated goat anti-mouse antibody (Invitrogen). Nuclei were stained with 4',6-diamidino-2-phenylindole (DAPI).

Example 7B

Automated Imaging and Enumeration of CTCs

This example describes the imaging and counting of circulating tumor cells captured by a microfluidic channel surface. An automated digital imaging system was designed to quantify the number of PSA-positive CTCs captured on the CTC-Chip. The imaging platform consisted of an upright fluorescence microscope (Eclipse 90i, Nikon) fitted with a high precision motorized stage (H102A ProScan II, Prior Scientific) and liquid light guide fluorescent system with built in DC power stabilization for consistent illumination (Lumen 200, Prior Scientific). Using a 10× objective (CFI Plan APO, Nikon), the entire footprint of the chip was imaged under three emission spectra (DAPI, FITC and Texas Red) with a 15 Bit, cooled CCD camera (Retiga 200R Fast 1394, QImaging) attached via a 1×-coupling lens. For consistency, all samples were imaged using fixed exposure times, based on the average signal intensity and background fluorescence levels from control samples. All chips were stored at 4° C. after staining and were scanned within 48 hours. The focal plane for each field of view was set using a multi-point planar surface approximation algorithm set prior to the initiation of the chip scan. Post-acquisition, images (~6,000 per chip for a multi-plane scan) were analyzed using a custom program developed in LabView 8.5 with IMAQ 3.5 (National Instruments, Austin, Tex.).

For analysis, all images were converted to a binary format using an absolute intensity threshold for segmentation. All resulting segments were filtered against pre-set criteria for positive events based on area and morphology. Segments or cells were determined to be positive for both cytokeratin 7/8 and DNA (CK+CTC) when the center of mass of each signal co-localized within 2.5 μm or |(x1, y1) DNA−(x2,y2) PSA|≤2.5 μm. Data obtained from the automated image analysis program was initially compared against manual counts obtained from multiple observers (n=4). Detection algorithms were adjusted until blinded manual counts were within 10% agreement of automated calculations. For each chip analyzed, an electronic data report was generated and an image data set was created, with target cells highlighted for quick review.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of selectively capturing an analytes from a fluid sample, the method comprising:
   contacting the sample with analyte binding moieties that selectively bind to the analytes;

separating first components of the sample including a majority of the analytes bound to the binding moieties from second components of the sample using size-based separation;

adding to the first components of the sample a plurality of binding agents under conditions that enable the plurality of the binding agents to be linked to the analyte binding moieties to form multivalent tagging agents bound to the analytes;

passing the first components of the sample past a surface to which is attached a plurality of capture agents that selectively bind to the binding agents; and capturing the analytes by providing conditions that enable the multivalent tagging agents bound to the analytes to bind to one or more of the capture agents.

2. A method of selectively capturing tumor cells from whole blood, the method comprising:

contacting the whole blood with a binding moiety that selectively binds to an antigen expressed on a surface of the tumor cells and not on a surface of normal cells to form tumor cell-binding moiety complexes;

separating a first subsample comprising tumor cell-binding moiety complexes and white blood cells from a second subsample comprising red blood cells, platelets, and unbound binding moiety using size-based separation;

adding to the first subsample a plurality of binding agents under conditions that enable the plurality of the binding agents to be linked to the binding moieties bound to the tumor cells;

passing the first subsample past a surface to which is attached a plurality of capture agents that selectively bind to the binding agents; and capturing the tumor cells by providing conditions that enable the binding agents bound to the tumor cells to bind to one or more of the capture agents.

3. The method of claim 1, wherein the binding moieties comprises an antibody bound to Horse Radish Peroxidase (HRP).

4. The method claim 1, wherein the analytes comprise cells.

5. The method of claim 4, wherein the cells express Epithelial Cell Adhesion Molecule (EpCAM).

6. The method of claim 2, wherein the antigen expressed on a surface of the tumor cells is Epithelial Cell Adhesion Molecule (EpCAM).

7. The method of claim 1, wherein the binding agents comprise tyramide-biotin molecules.

8. The method of claim 7, wherein the capture agents comprise a ligand that binds to biotin.

9. The method of claim 1, wherein the surface forms at least a portion of a microfluidic channel.

10. The method of claim 2, wherein the tumor cells have a concentration of less than about $10^{-6}$/mL in the whole blood.

11. The method of claim 9, wherein the surface is an outer surface of a post within the channel, the post extending partially across the channel in a direction perpendicular to a direction of fluid flow of the biological sample within the channel.

12. The method of claim 1, wherein the fluid sample comprises blood.

13. The method of claim 12, wherein the first components of the biological sample comprise white blood cells.

14. The method of claim 1, further comprising separating unbound analyte binding moieties from the first components of the sample while separating the first components of the sample from the second components of the sample.

15. The method of claim 1, wherein the binding agents comprise biotin and the capture agents bind to biotin.

16. The method of claim 1, wherein the analytes comprise cells having a concentration of less than about $10^{-6}$/mL in the sample.

17. The method of claim 2, wherein the binding agents comprise tyramide-biotin molecules.

18. The method of claim 1, wherein the plurality of binding agents are linked to the analyte binding moieties via dendrimer molecules to form the multivalent tagging agents.

19. The method of claim 18, wherein the dendrimer molecules each comprise dozens to hundreds of possible sites to which the binding agents can be coupled.

20. The method of claim 18, wherein the binding agents are biotin molecules.

21. The method of claim 1, further comprising applying a detergent to the surface to reduce non-specific binding.

22. The method of claim 1, wherein the analytes are selected from the group consisting of circulating tumor cells, endothelial cells, fetal cells, bacteria, viruses, protists, fungal cells, platelets, sickle cell red blood cells, and leukocytes.

* * * * *

UNITED STATES PATENT AND TRADEMARK OFFICE
CERTIFICATE OF CORRECTION

| | | |
|---|---|---|
| PATENT NO. | : 9,034,658 B2 | Page 1 of 1 |
| APPLICATION NO. | : 13/511536 | |
| DATED | : May 19, 2015 | |
| INVENTOR(S) | : Thomas A. Barber et al. | |

It is certified that error appears in the above-identified patent and that said Letters Patent is hereby corrected as shown below:

Claims

Column 32, Claim 1, Line 64:
After "capturing" delete "an"

Column 33, Claim 3, Line 36:
Delete "comprises" and Insert -- comprise --

Column 33, Claim 4, Line 38:
After "method" Insert -- of --

Column 34, Claim 22, Line 43:
Delete "sickle cell" and Insert -- sickle cell, --

Signed and Sealed this
Sixth Day of October, 2015

Michelle K. Lee
*Director of the United States Patent and Trademark Office*